(12) United States Patent
Boyanov et al.

(10) Patent No.: US 11,774,400 B2
(45) Date of Patent: *Oct. 3, 2023

(54) DEVICE FOR SEQUENCING

(71) Applicant: Illumina, Inc., San Diego, CA (US)

(72) Inventors: Boyan Boyanov, San Diego, CA (US); Jens Gundlach, Seattle, WA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/828,991

(22) Filed: May 31, 2022

(65) Prior Publication Data
US 2022/0299469 A1     Sep. 22, 2022

Related U.S. Application Data

(63) Continuation of application No. 16/626,011, filed as application No. PCT/US2019/017814 on Feb. 13, 2019, now Pat. No. 11,391,693.
(Continued)

(51) Int. Cl.
*G01N 27/414* (2006.01)
*G01N 33/487* (2006.01)
(Continued)

(52) U.S. Cl.
CPC ..... *G01N 27/4145* (2013.01); *G01N 27/4146* (2013.01); *G01N 33/48721* (2013.01);
(Continued)

(58) Field of Classification Search
None
See application file for complete search history.

(56) References Cited

U.S. PATENT DOCUMENTS

| 6,413,792 B1 | 7/2002 | Sauer et al. |
| 7,279,337 B2 | 10/2007 | Zhu |

(Continued)

FOREIGN PATENT DOCUMENTS

| CA | 2790666 A1 | 9/2011 |
| CA | 2956794 A1 | 2/2016 |

(Continued)

OTHER PUBLICATIONS

Huang, S., "Nanopore-Based Sensing Devices and Applications to Genome Sequencing: A Brief History and the Missing Pieces", Chinese Science Bulletin, vol. 59, No. 35, pp. 4918-4928, 2014.
(Continued)

*Primary Examiner* — J. Christopher Ball
(74) *Attorney, Agent, or Firm* — Dierker & Kavanaugh, P.C.

(57) ABSTRACT

Example devices include a cis well associated with a cis electrode, a trans well associated with a trans electrode, and a field effect transistor (FET) positioned between the cis well and the trans well. Examples of the field effect transistor (FET) include a fluidic system defined therein. The fluidic system includes a first cavity facing the cis well, a second cavity fluidically connected to the trans well, and a through via extending through the field effect transistor from the first cavity. A first nanoscale opening fluidically connects the cis well and the first cavity, the first nanoscale opening having an inner diameter. A second nanoscale opening fluidically connects the through via and the second cavity, the second nanoscale opening having an inner diameter. The second nanoscale opening inner diameter is larger than the first nanoscale opening inner diameter.

20 Claims, 13 Drawing Sheets

Related U.S. Application Data

(60) Provisional application No. 62/710,350, filed on Feb. 16, 2018.

(51) Int. Cl.
    *H01L 21/74*     (2006.01)
    *H01L 29/66*     (2006.01)
    *H01L 29/786*     (2006.01)

(52) U.S. Cl.
    CPC ...... *H01L 21/743* (2013.01); *H01L 29/66772* (2013.01); *H01L 29/78696* (2013.01)

(56) References Cited

U.S. PATENT DOCUMENTS

| | | |
|---|---|---|
| 8,628,919 B2 | 1/2014 | Xiao et al. |
| 8,669,124 B2 | 3/2014 | Merz |
| 8,698,481 B2 | 4/2014 | Lieber et al. |
| 8,961,763 B2 | 2/2015 | Dunbar et al. |
| 8,986,928 B2 | 3/2015 | Emig et al. |
| 9,017,937 B1 | 4/2015 | Turner et al. |
| 9,063,081 B2 | 6/2015 | Sauer et al. |
| 9,696,277 B2 | 7/2017 | Dunbar et al. |
| 9,863,912 B2 | 1/2018 | Dunbar et al. |
| 10,488,394 B2 | 11/2019 | Liu et al. |
| 11,054,390 B2 | 7/2021 | Dunbar et al. |
| 11,391,693 B2 * | 7/2022 | Boyanov ............ G01N 27/3278 |
| 2010/0327847 A1 | 12/2010 | Leiber et al. |
| 2013/0240359 A1 | 9/2013 | Turner et al. |
| 2014/0174927 A1 | 6/2014 | Bashir et al. |
| 2016/0116435 A1 | 4/2016 | Cheng et al. |
| 2016/0231307 A1 | 8/2016 | Xie |
| 2017/0138925 A1 | 5/2017 | Kim et al. |
| 2017/0227494 A1 | 8/2017 | Gundlach et al. |
| 2017/0318966 A1 | 11/2017 | Chen |
| 2019/0011424 A1 | 1/2019 | Mcruer et al. |
| 2019/0094180 A1 | 3/2019 | Yanagi |

FOREIGN PATENT DOCUMENTS

| | | |
|---|---|---|
| CA | 2984112 A1 | 11/2016 |
| CN | 105637081 A | 6/2016 |
| EP | 2411536 B1 | 9/2014 |
| JP | 2014190891 A | 10/2014 |
| JP | 2017523424 A | 8/2017 |
| WO | 0181896 A1 | 11/2001 |
| WO | 0181908 A1 | 11/2001 |
| WO | 2009035647 A1 | 3/2009 |
| WO | 2013016486 A1 | 1/2013 |
| WO | 2016183218 A1 | 11/2016 |
| WO | 2017184790 A1 | 10/2017 |
| WO | 2017187588 A1 | 11/2017 |

OTHER PUBLICATIONS

Magierowski, S. et al., "Nanopore-CMOS Interfaces for DNA Sequencing", Biosensors, vol. 6, Article 42, pp. 1-28, 2016.

ISA, "International Search Report and Written Opinion for International Application No. PCT/US2019/017814", 15 pages, Jun. 4, 2019.

* cited by examiner

DEVICE FOR SEQUENCING

CROSS-REFERENCE TO RELATED APPLICATIONS

This application is a continuation of U.S. application Ser. No. 16/626,011, filed Dec. 23, 2019, which itself is a national stage entry under 35 U.S.C. § 371 of PCT/US2019/017814, filed Feb. 13, 2019, which itself claims the benefit of U.S. Provisional Application Ser. No. 62/710,350, filed Feb. 16, 2018, the content of each of which is incorporated by reference herein in its entirety.

BACKGROUND

Various polynucleotide sequencing techniques involve performing a large number of controlled reactions on local support surfaces or within predefined reaction chambers. The designated reactions may then be observed or detected, and subsequent analysis may help identify or reveal properties of the polynucleotide involved in the reaction. Another polynucleotide sequencing technique has been developed that utilizes a nanopore, which can provide a channel for an ionic electrical current. A polynucleotide is driven through the nanopore, and as the polynucleotide passes through the nanopore, it disrupts the electrical current through the nanopore. Each passing nucleotide, or series of nucleotides, yields a characteristic electrical current, and the record of the current levels corresponds to the sequence of the polynucleotide.

SUMMARY

A first aspect disclosed herein is a device. In an example, the device comprises a cis well associated with a cis electrode; a trans well associated with a trans electrode; a field effect transistor (FET) positioned between the cis well and the trans well, the field effect transistor (FET) including: a fluidic system defined therein, the fluidic system including, a first cavity facing the cis well; a second cavity fluidically connected to the trans well, and a through via extending through the field effect transistor from the first cavity; a first nanoscale opening fluidically connecting the cis well and the first cavity, the first nanoscale opening having an inner diameter; and a second nanoscale opening fluidically connecting the through via and the second cavity, the second nanoscale opening having an inner diameter, wherein the second nanoscale opening inner diameter is larger than the first nanoscale opening inner diameter.

In an example of the device, the second nanoscale opening inner diameter is at least about two times larger than the first nanoscale opening inner diameter; the first nanoscale opening inner diameter ranges from about 1 nm to about 3 nm; and the second nanoscale opening inner diameter ranges from about 2 nm to about 20 nm.

In an example of the device, the second nanoscale opening inner diameter ranges from about two times larger than the first nanoscale opening inner diameter to about five times larger than the first nanoscale opening inner diameter.

In an example of the device, the first nanoscale opening inner diameter ranges from about 0.5 nm to about 3 nm; and the second nanoscale opening inner diameter ranges from about 10 nm to about 20 nm.

In an example of the device, the second nanoscale opening inner diameter is about three times larger than the first nanoscale opening inner diameter; the first nanoscale opening inner diameter ranges from about 1 nm to about 2 nm; and the second nanoscale opening inner diameter ranges from about 10 nm to about 20 nm.

An example of the device further comprises a membrane positioned between the cis well and the first cavity, wherein the first nanoscale opening extends through the membrane. As one example, the membrane may be selected from the group consisting of a lipid and a biomimetic equivalent of a lipid. In this one example, the first nanoscale opening extends through: a polynucleotide nanopore; a polypeptide nanopore; or a carbon nanotube, disposed in the membrane. As another example, the membrane is a synthetic membrane, and the first nanoscale opening is a solid state nanopore.

In an example of the device, the first nanoscale opening has a variable electrical resistance; and the second nanoscale opening has an at least substantially fixed electrical resistance.

In an example, the device comprises a nanopore sequencer. In this example, an array may include a plurality of the nanopore sequencers, and wherein: each of the plurality of the nanopore sequencers shares a common cis electrode and a common trans electrode; or each of the plurality of the nanopore sequencers has a distinct cis electrode and a distinct trans electrode; or each of the plurality of the nanopore sequencers shares a common cis electrode and has a distinct trans electrode; or each of the plurality of the nanopore sequencers has a distinct cis electrode and shares a common trans electrode.

It is to be understood that any features of the device and/or of the array disclosed herein may be combined together in any desirable manner and/or configuration.

A second aspect disclosed herein is a method of using examples of the device disclosed herein. In an example, the method of using the device comprises introducing an electrolyte into each of the cis well, the trans well, the first cavity, the FET through via, and the second cavity; applying a voltage bias between the cis electrode and the trans electrode sufficient to drive a polynucleotide through the first nanoscale opening, wherein an electrical resistance of the first nanoscale opening varies in response to an identity of bases in the polynucleotide, and wherein a potential of the electrolyte in the FET through via varies in response to the variation in electrical resistance of the first nanoscale opening; and measuring a response of the FET as the polynucleotide is driven through the first nanoscale opening, to identify the bases in the polynucleotide.

In an example of the method of using the device, the FET further comprises a source, a drain, and a channel, and wherein measuring the response of the FET includes: measuring a source-drain current; or measuring a potential at the source, the drain, or both the source and the drain; or measuring a resistance of the channel; or combinations thereof.

It is to be understood that any features of the method of using the device may be combined together in any desirable manner. Moreover, it is to be understood that any combination of features of this method and/or of the device and/or of the array may be used together, and/or may be combined with any of the examples disclosed herein.

A third aspect disclosed herein is a method. In an example, the method comprises fabricating a field effect transistor; defining a fluidic system therein, the fluidic system including a first cavity having an inlet end and an outlet end, and a second cavity opposed to the first cavity; defining a through via through the field effect transistor from the first cavity outlet end toward the second cavity; defining a membrane over the inlet end of the first cavity, the membrane having a first nanoscale opening therethrough, the first nanoscale opening having an inner diameter; and defining a second nanoscale opening through a base substrate of the field effect transistor to fluidically connect the through via with the second cavity, the second nanoscale opening having an inner diameter, wherein the second nanoscale opening inner diameter is larger than the first nanoscale opening inner diameter.

An example of the method further comprises fluidically connecting a cis well to the first nanoscale opening, the cis well being associated with a cis electrode; fluidically connecting a trans well to the second cavity, the trans well being associated with a trans electrode, thereby forming a nanopore sequencer; and immersing the nanopore sequencer into an electrolyte.

In an example of the method, fabricating the field effect transistor comprises defining a source, a drain, and a channel in a silicon layer of a silicon on insulator substrate; oxidizing a surface of the silicon layer to form a gate oxide on the source, the drain, and the channel; forming a sacrificial layer on the gate oxide on the channel; depositing an etch stop material to form a layer on the gate oxide on the source and on the drain and on the sacrificial layer and to form the base substrate; and fabricating a vertical interconnect access (via) and a metallic interconnect partially encapsulated in an insulating material, the via electrically connecting the source and drain to the metallic interconnects.

In this example, prior to depositing the etch stop material, the method further comprises defining the second cavity of the fluidic system by etching a portion of the second silicon layer through to an insulator layer of the silicon on insulator substrate, wherein the portion etched away is opposed to the channel.

In this example, the etch stop material is a solid state material that is deposited on the second silicon layer and an exposed portion of the insulator layer to form the base substrate. In this example, the second nanoscale opening is defined by etching through a portion of the solid state material.

Also in this example, defining the first cavity may comprise etching an area of the insulating material through to the sacrificial layer, wherein the area abuts the channel, and etching the sacrificial layer to expose the gate oxide on the channel; and defining the through via may comprise etching through respective portions of each of the gate oxide, the silicon layer of the silicon on insulator substrate, and the insulating layer of the silicon on insulator substrate to expose the solid state material. This example of the method may further comprise oxidizing exposed portions of the silicon layer of the silicon on insulator substrate in the through via. This example of the method may further comprise depositing or growing an insulating layer on exposed portions of the silicon layer of the silicon on insulator substrate in the through via.

It is to be understood that any features of this method may be combined together in any desirable manner. Moreover, it is to be understood that any combination of features of this method and/or of the method of using the device and/or of the device and/or of the array may be used together, and/or may be combined with any of the examples disclosed herein.

Still further, it is to be understood that any feature or combination of features of any of the devices and/or of the arrays and/or of any of the methods may be combined together in any desirable manner, and/or may be combined with any of the examples disclosed herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1B:
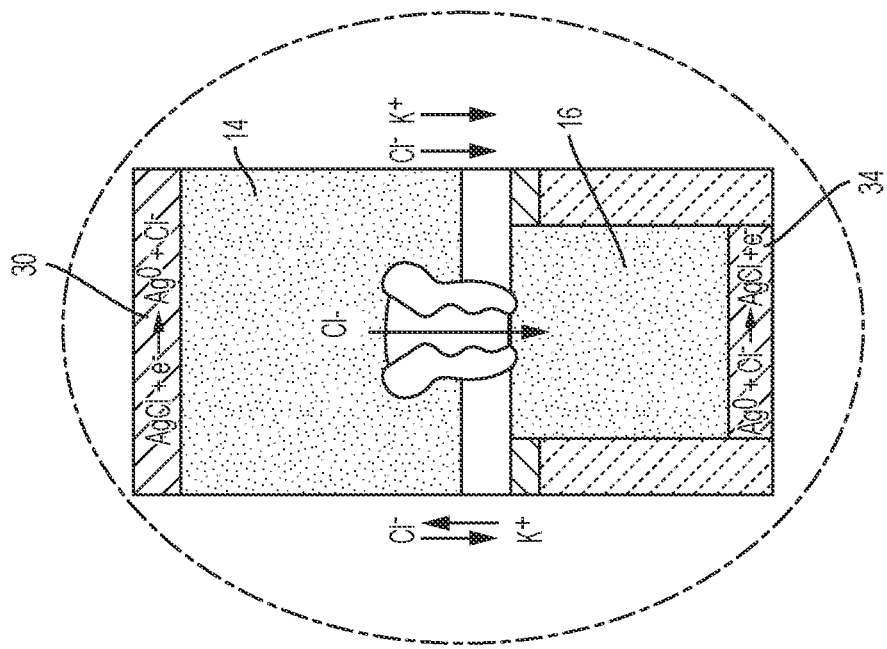
FIG. 1B is an enlarged view of the section of FIG. 1A denoted "See FIG. 1B", schematically showing the balance of ionic flow in the nanopore sensor of FIG. 1A.
Figure 1A:
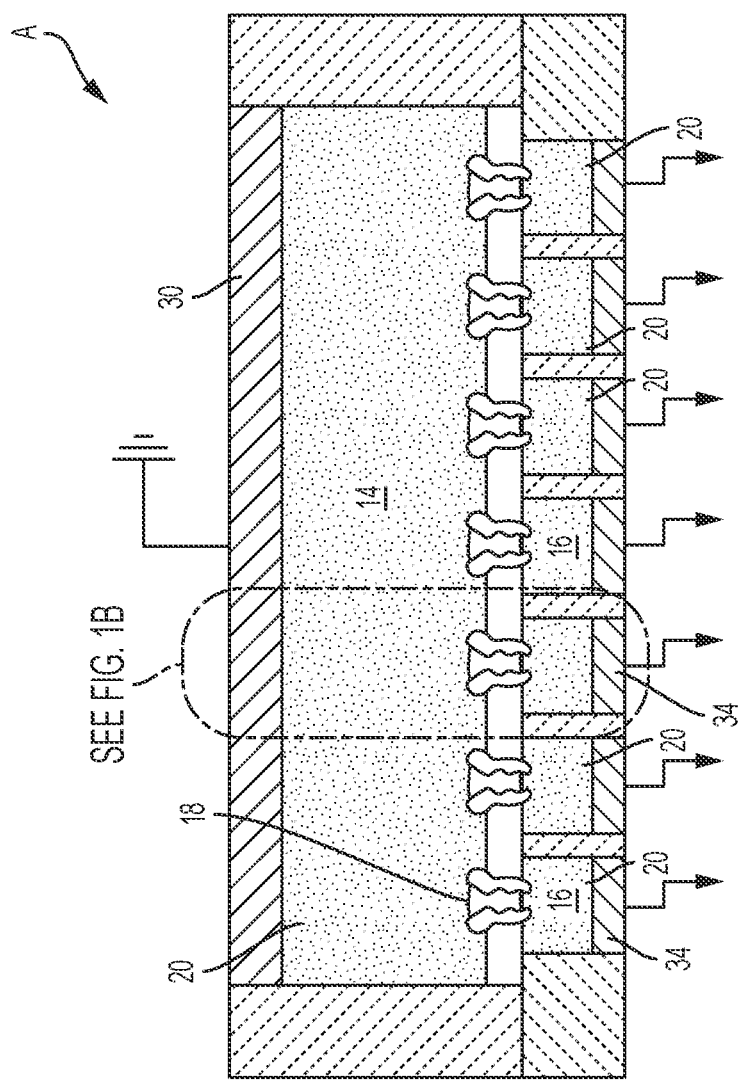
FIG. 1A is a schematic and partially cross-sectional view of a nanopore sensor array without field effect transistors incorporated therein.

A schematic and partially cross-sectional view of a nanopore sensor array A is shown in FIG. 1A. The nanopore sensor array A includes a common cis well 14 with a cis/top electrode 30 and an array of trans wells 16 with individually addressable trans/bottom electrodes 34. Nanopores 18 fluidically connect the cis well 14 and the respective trans wells 16, and an electrolyte 20 is in the cis well 14 and the trans wells 16. Current passes through each nanopore 18 and is measured by the bottom electrodes 34.

The use of individually addressable trans electrodes may, in some instances, limit the scalability of the architecture shown in FIG. 1A. An example of the relevant electrochemical half-reactions at the electrodes are:

Cis (cathode): $AgCl + e^- \rightarrow Ag^0 + Cl^-$; and

Trans (anode): $Ag^0 + Cl^- \rightarrow AgCl + e^-$.

For every unit charge of current, one Cl atom is consumed at the trans electrode. However, the current carried by the nanopore 18 consists equally of $K^+$ and $Cl^-$ ions. This causes an imbalance between the supply and consumption of $Cl^-$ in the trans well, as schematically illustrated in FIG. 1B.

Figure 5:
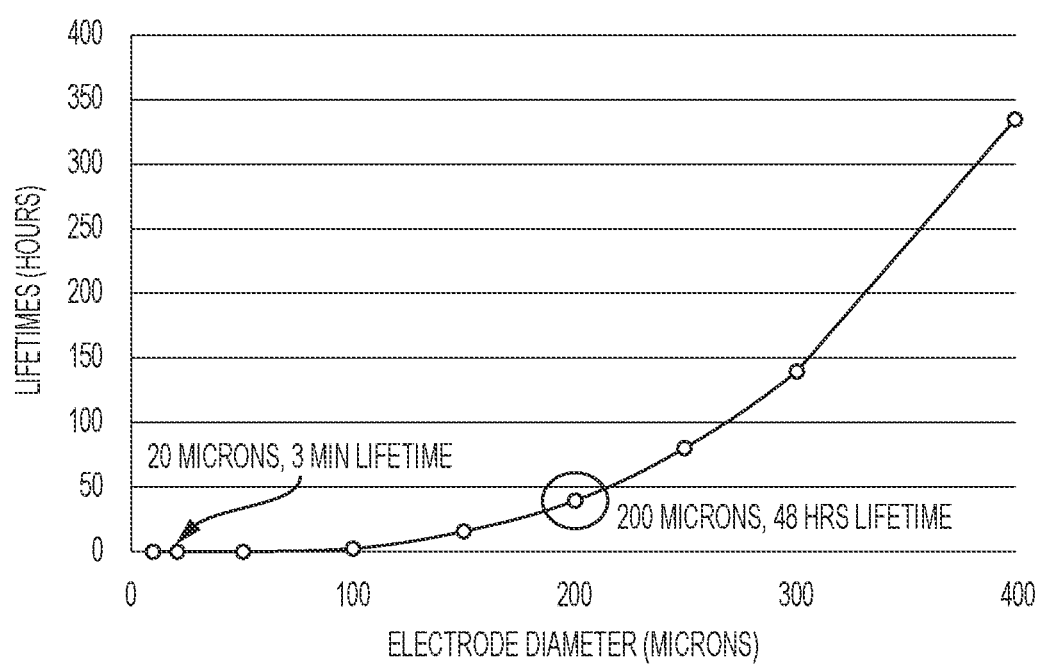
FIG. 5 is a graph illustrating lifetime (in hours, Y-axis) versus electrode diameter (in microns, X-axis)

Over time, $Cl^-$ in the trans well is depleted by the electrochemical reactions to pass current. As the sensor array A is scaled, the volume of each trans well 16 typically depletes as the $3^{rd}$ power of the well dimension (assuming that a constant aspect ratio is maintained). The resulting decrease in the usable lifetime of the sensor array A may be significant, as shown in FIG. 5. In order to achieve a practical sensor lifetime (e.g., about 48 hours) the diameter of the trans well would be maintained above 100 µm. However, as the pitch of the circuitry used to measure the currents can be reduced to 10 μm or less, the overall scalability of the sensor array A may be limited by the need to pass a current.

Though the discussion above is in terms of a Ag/AgCl electrode in NaCl or KCl solution, it is to be understood that these considerations apply for any electrode/electrolyte pair that may be used to pass the current. There will be electrolyte consumption on the trans electrode 34, and the volume of available electrolyte 20 is a limiting factor in the lifetime of the sensor array A.

As described in further detail below, examples of the device and method according to the present disclosure incorporate a FET and do not need to include individually addressable trans wells and electrodes. As such, the trans well(s) according to examples of the present disclosure may be much larger than the trans wells of sensor array A, thereby allowing for desirable scaling to improve device lifetime.

The technique of nanopore sequencing uses variations in current to distinguish nucleotide bases. As mentioned above, in nanopore sequencers, one electrolyte redox reagent may be partially consumed on a trans well (or chamber) electrode in order to support Faradaic current through the system. The partially consumed electrolyte redox reagent may not be efficiently replenished on a corresponding cis well electrode, due, in part, to ion transport inhibition through the nanopore(s). For example, chloride anions may be partially depleted on the trans side due to plating and may not be fully replenished on the cis side. A concentration gradient develops for both of the electrolyte redox reagents (e.g., cation and anion), and a new equilibrium is established at a much lower concentration of the partially depleted reagent on the trans side. The imbalance of electrolyte redox reagent transport through the nanopore versus the partial consumption of one of the reagents on the trans electrode can cause current drift, which can deleteriously affect the ability to distinguish between nucleotide bases, as shown in FIG. 1B.

The partial consumption of the electrolyte redox reagent depends on several factors, including the starting concentration of the electrolyte redox reagent, the current that passes through the nanopore, and the size of the trans chamber (e.g., larger chambers are generally associated with less reagent consumption and smaller chambers are generally associated with more reagent consumption).

Partial consumption may be evidenced by a reduction in the initial reagent concentration, where the reduction is greater than a factor of 10. In some instances, the reduction ranges from a factor of 20 to a factor of 100. For example, the chloride concentration of an electrolyte having an initial chloride concentration of about 300 mM in a 10 μm trans well can be depleted to about 10 mM, and thus the initial concentration is reduced by a factor of about 30. For another example, the chloride concentration of an electrolyte having an initial chloride concentration of about 10 mM in a 10 μm trans well can be depleted to about 0.1 mM, and thus the initial concentration is reduced by a factor of about 100. It is to be understood that the partial consumption/depletion can approach 100% (i.e., the electrolyte redox reagent remaining in the system approaches 0%), but an equilibrium will establish between the electrolyte redox reagents, even at such low levels of the partially consumed reagent.

As mentioned above, the technique of nanopore sequencing uses variations in current to distinguish nucleotide bases. A depletion in the electrolyte species results in a reduction (or undesirable shift) in current, which deleteriously affects the ability to obtain accurate current readings for the nucleotide bases. The ability to have larger trans chambers/wells made possible by example devices of the present disclosure leads to more of the reagent being present over time (e.g., compared to the example sensor array A referred to above). As such, the effect of the consumption or depletion of the reagent is minimized, current drift is mitigated, and the lifetime of the electrolyte, the trans electrode, and the trans well is increased. Thus, examples of the device for sequencing and method disclosed herein extend the lifetime of the example device (see, e.g., FIG. 5) and enable greater than 100× (100 times) reduction in the density of the sensor array.

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad. Moreover, unless explicitly stated to the contrary, examples comprising, including, or having an element or a plurality of elements having a particular property may include additional elements, whether or not the additional elements have that property.

As used herein, the terms "fluidically connecting," "fluid communication," "fluidically coupled," and the like refer to two spatial regions being connected together such that a liquid or gas may flow between the two spatial regions. For example, a cis well/wells may be fluidically connected to a trans well/wells by way of a first cavity, a through via, and a second cavity, such that at least a portion of an electrolyte may flow between the connected wells. The two spatial regions may be in fluid communication through first and second nanoscale openings, or through one or more valves, restrictors, or other fluidic components that are to control or regulate a flow of fluid through a system.

As used herein, the term "interstitial region" refers to an area in a substrate/solid support or a membrane, or an area on a surface that separates other areas, regions, features associated with the support or membrane or surface. For example, an interstitial region of a membrane can separate one nanopore of an array from another nanopore of the array. For another example, an interstitial region of a substrate can separate one trans well from another trans well. The two areas that are separated from each other can be discrete, i.e., lacking physical contact with each other. In many examples, the interstitial region is continuous whereas the areas are discrete, for example, as is the case for a plurality of nanopores defined in an otherwise continuous membrane, or for a plurality of wells defined in an otherwise continuous substrate/support. The separation provided by an interstitial region can be partial or full separation. Interstitial regions may have a surface material that differs from the surface material of the features defined in the surface. For example, the surface material at the interstitial regions may be a lipid material, and a nanopore formed in the lipid material can have an amount or concentration of polypeptide that exceeds the amount or concentration present at the interstitial regions. In some examples, the polypeptide may not be present at the interstitial regions.

As used herein, the term "membrane" refers to a non-permeable or semi-permeable barrier or other sheet that separates two liquid/gel chambers (e.g., a cis well and a fluidic cavity) which can contain the same compositions or different compositions therein. The permeability of the membrane to any given species depends upon the nature of the membrane. In some examples, the membrane may be non-permeable to ions, to electric current, and/or to fluids.

For example, a lipid membrane may be impermeable to ions (i.e., does not allow any ion transport therethrough), but may be at least partially permeable to water (e.g., water diffusivity ranges from about 40 µm/s to about 100 µm/s). For another example, a synthetic/solid state membrane, one example of which is silicon nitride, may be impermeable to ions, electric charge, and fluids (i.e., the diffusion of all of these species is zero). Any membrane may be used in accordance with the present disclosure, as long as the membrane can include a transmembrane nanoscale opening and can maintain a potential difference across the membrane. The membrane may be a monolayer or a multilayer membrane. A multilayer membrane includes two or more layers, each of which is a non-permeable or semi-permeable material.

The membrane may be formed of materials of biological or non-biological origin. A material that is of biological origin refers to material derived from or isolated from a biological environment such as an organism or cell, or a synthetically manufactured version of a biologically available structure (e.g., a biomimetic material).

An example membrane that is made from the material of biological origin includes a monolayer formed by a bola-lipid. Another example membrane that is made from the material of biological origin includes a lipid bilayer. Suitable lipid bilayers include, for example, a membrane of a cell, a membrane of an organelle, a liposome, a planar lipid bilayer, and a supported lipid bilayer. A lipid bilayer can be formed, for example, from two opposing layers of phospholipids, which are arranged such that their hydrophobic tail groups face towards each other to form a hydrophobic interior, whereas the hydrophilic head groups of the lipids face outwards towards the aqueous environment on each side of the bilayer. Lipid bilayers also can be formed, for example, by a method in which a lipid monolayer is carried on an aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has at least partially evaporated, the solution/air interfaces on either side of the aperture are physically moved up and down past the aperture until a bilayer is formed. Other suitable methods of bilayer formation include tip-dipping, painting bilayers, and patch-clamping of liposome bilayers. Any other methods for obtaining or generating lipid bilayers may also be used.

A material that is not of biological origin may also be used as the membrane. Some of these materials are solid state materials and can form a solid state membrane, and others of these materials can form a thin liquid film or membrane. The solid state membrane can be a monolayer, such as a coating or film on a supporting substrate (i.e., a solid support), or a free-standing element. The solid state membrane can also be a composite of multilayered materials in a sandwich configuration. Any material not of biological origin may be used, as long as the resulting membrane can include a transmembrane nanoscale opening and can maintain a potential difference across the membrane. The membranes may include organic materials, inorganic materials, or both. Examples of suitable solid state materials include, for example, microelectronic materials, insulating materials (e.g., silicon nitride ($Si_3N_4$), aluminum oxide ($Al_2O_3$), hafnium oxide ($HfO_2$), tantalum pentoxide ($Ta_2O_5$), silicon oxide ($SiO_2$), etc.), some organic and inorganic polymers (e.g., polyamide, plastics, such as polytetrafluoroethylene (PTFE), or elastomers, such as two-component addition-cure silicone rubber), and glasses. In addition, the solid state membrane can be made from a monolayer of graphene, which is an atomically thin sheet of carbon atoms densely packed into a two-dimensional honeycomb lattice, a multilayer of graphene, or one or more layers of graphene mixed with one or more layers of other solid state materials. A graphene-containing solid state membrane can include at least one graphene layer that is a graphene nanoribbon or graphene nanogap, which can be used as an electrical sensor to characterize the target polynucleotide. It is to be understood that the solid state membrane can be made by any suitable method, for example, chemical vapor deposition (CVD). In an example, a graphene membrane can be prepared through either CVD or exfoliation from graphite. Examples of suitable thin liquid film materials that may be used include diblock copolymers or triblock copolymers, such as amphiphilic PMOXA-PDMS-PMOXA ABA triblock copolymers.

As used herein, the term "nanopore" is intended to mean a hollow structure discrete from, or defined in, and extending across the membrane that permits ions, electric current, and/or fluids to cross from one side of the membrane to the other side of the membrane. For example, a membrane that inhibits the passage of ions or water soluble molecules can include a nanopore structure that extends across the membrane to permit the passage (through a nanoscale opening/channel extending through the nanopore structure) of the ions or water soluble molecules from one side of the membrane to the other side of the membrane. The diameter of the nanoscale opening/channel extending through the nanopore structure can vary along its length (i.e., from one side of the membrane to the other side of the membrane), but at any point is on the nanoscale (i.e., from about 1 nm to about 100 nm, or to less than 1000 nm). Examples of the nanopore include, for example, biological nanopores, solid state nanopores, and biological and solid state hybrid nanopores.

As used herein, the term "diameter" is intended to mean a longest straight line inscribable in a cross-section of a nanoscale opening through a centroid of the cross-section of the nanoscale opening. It is to be understood that the nanoscale opening may or may not have a circular or substantially circular cross-section (the cross-section of the nanoscale opening being substantially parallel with the cis/trans electrodes). Further, the cross-section may be regularly or irregularly shaped.

As used herein, the term "biological nanopore" is intended to mean a nanopore whose structure portion is made from materials of biological origin. Biological origin refers to a material derived from or isolated from a biological environment such as an organism or cell, or a synthetically manufactured version of a biologically available structure. Biological nanopores include, for example, polypeptide nanopores and polynucleotide nanopores.

As used herein, the term "polypeptide nanopore" is intended to mean a protein/polypeptide that extends across the membrane, and permits ions, electric current, and/or fluids to flow therethrough from one side of the membrane to the other side of the membrane. A polypeptide nanopore can be a monomer, a homopolymer, or a heteropolymer. Structures of polypeptide nanopores include, for example, an α-helix bundle nanopore and a β-barrel nanopore. Example polypeptide nanopores include α-hemolysin, *Mycobacterium smegmatis* porin A (MspA), gramicidin A, maltoporin, OmpF, OmpC, PhoE, Tsx, F-pilus, etc. The protein α-hemolysin is found naturally in cell membranes, where it acts as a channel for ions or molecules to be transported in and out of cells. *Mycobacterium smegmatis* porin A (MspA) is a membrane porin produced by Mycobacteria, which allows hydrophilic molecules to enter the bacterium. MspA forms a tightly interconnected octamer and transmembrane beta-barrel that resembles a goblet and contains a central channel/pore.

A polypeptide nanopore can be synthetic. A synthetic polypeptide nanopore includes a protein-like amino acid sequence that does not occur in nature. The protein-like amino acid sequence may include some of the amino acids that are known to exist but do not form the basis of proteins (i.e., non-proteinogenic amino acids). The protein-like amino acid sequence may be artificially synthesized rather than expressed in an organism and then purified/isolated.

As used herein, the term "polynucleotide nanopore" is intended to include a polynucleotide that extends across the membrane, and permits ions, electric current, and/or fluids to flow from one side of the membrane to the other side of the membrane. A polynucleotide pore can include, for example, a polynucleotide origami (e.g., nanoscale folding of DNA to create the nanopore).

Also as used herein, the term "solid state nanopore" is intended to mean a nanopore whose structure portion is defined by a solid state membrane and includes materials of non-biological origin (i.e., not of biological origin). A solid-state nanopore can be formed of an inorganic or organic material. Solid state nanopores include, for example, silicon nitride nanopores, silicon dioxide nanopores, and graphene nanopores.

The nanopores disclosed herein may be hybrid nanopores. A "hybrid nanopore" refers to a nanopore including materials of both biological and non-biological origins. An example of a hybrid nanopore includes a polypeptide-solid state hybrid nanopore and a polynucleotide-solid state nanopore.

As used herein, the term "nanopore sequencer" refers to any of the devices disclosed herein that can be used for nanopore sequencing. In the examples disclosed herein, during nanopore sequencing, the nanopore is immersed in example(s) of the electrolyte disclosed herein and a potential difference is applied across the membrane. In an example, the potential difference is an electric potential difference or an electrochemical potential difference. An electrical potential difference can be imposed across the membrane via a voltage source that injects or administers current to at least one of the ions of the electrolyte contained in the cis well or one or more of the trans wells. An electrochemical potential difference can be established by a difference in ionic composition of the cis and trans wells in combination with an electrical potential. The different ionic composition can be, for example, different ions in each well or different concentrations of the same ions in each well.

The application of the potential difference across the nanopores may force the translocation of a nucleic acid through the first nanoscale opening 23 (shown, e.g., in FIG. 2A and described in more detail below). One or more signals are generated that correspond to the translocation of the nucleotide through the nanopore. Accordingly, as a target polynucleotide, or as a mononucleotide or a probe derived from the target polynucleotide or mononucleotide, transits through the nanopore, the current across the membrane changes due to base-dependent (or probe dependent) blockage of the constriction, for example. The signal from that change in current can be measured using any of a variety of methods. Each signal is unique to the species of nucleotide(s) (or probe) in the nanopore, such that the resultant signal can be used to determine a characteristic of the polynucleotide. For example, the identity of one or more species of nucleotide(s) (or probe) that produces a characteristic signal can be determined.

As used herein, a "nucleotide" includes a nitrogen containing heterocyclic base, a sugar, and one or more phosphate groups. Nucleotides are monomeric units of a nucleic acid sequence. Examples of nucleotides include, for example, ribonucleotides or deoxyribonucleotides. In ribonucleotides (RNA), the sugar is a ribose, and in deoxyribonucleotides (DNA), the sugar is a deoxyribose, i.e., a sugar lacking a hydroxyl group that is present at the 2' position in ribose. The nitrogen containing heterocyclic base can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. The phosphate groups may be in the mono-, di-, or tri-phosphate form. These nucleotides are natural nucleotides, but it is to be further understood that non-natural nucleotides, modified nucleotides or analogs of the aforementioned nucleotides can also be used.

As used herein, the term "signal" is intended to mean an indicator that represents information. Signals include, for example, an electrical signal and an optical signal. The term "electrical signal" refers to an indicator of an electrical quality that represents information. The indicator can be, for example, current, voltage, tunneling, resistance, potential, voltage, conductance, or a transverse electrical effect. An "electronic current" or "electric current" refers to a flow of electric charge. In an example, an electrical signal may be an electric current passing through a nanopore, and the electric current may flow when an electric potential difference is applied across the nanopore.

The term "substrate" refers to a rigid, solid support that is insoluble in aqueous liquid and is incapable of passing a liquid absent an aperture, port, or other like liquid conduit. In the examples disclosed herein, the substrate may have wells or chambers defined therein. Examples of suitable substrates include glass and modified or functionalized glass, plastics (including acrylics, polystyrene and copolymers of styrene and other materials, polypropylene, polyethylene, polybutylene, polyurethanes, polytetrafluoroethylene (PTFE) (such as TEFLON® from Chemours), cyclic olefins/cyclo-olefin polymers (COP) (such as ZEONOR® from Zeon), polyimides, etc.), nylon, ceramics, silica or silica-based materials, silicon and modified silicon, carbon, metals, inorganic glasses, and optical fiber bundles.

The terms top, bottom, lower, upper, on, etc. are used herein to describe the device/nanopore sequencer and/or the various components of the device. It is to be understood that these directional terms are not meant to imply a specific orientation, but are used to designate relative orientation between components. The use of directional terms should not be interpreted to limit the examples disclosed herein to any specific orientation(s).

As used herein, the terms "well", "cavity" and "chamber" are used synonymously, and refer to a discrete feature defined in the device that can contain a fluid (e.g., liquid, gel, gas). A cis well is a chamber that contains or is partially defined by a cis electrode, and is also fluidically connected to the fluidic system of a FET which in turn is fluidically connected to a trans well/chamber. Examples of an array of the present device may have one cis well or multiple cis wells. The trans well is a single chamber that contains or is partially defined by its own trans electrode, and is also fluidically connected to a cis well. In examples including multiple trans wells, each trans well is electrically isolated from each other trans well. Further, it is to be understood that the cross-section of a well taken parallel to a surface of a substrate at least partially defining the well can be curved, square, polygonal, hyperbolic, conical, angular, etc.

The aspects and examples set forth herein and recited in the claims can be understood in view of the above definitions.

Figure 2A:
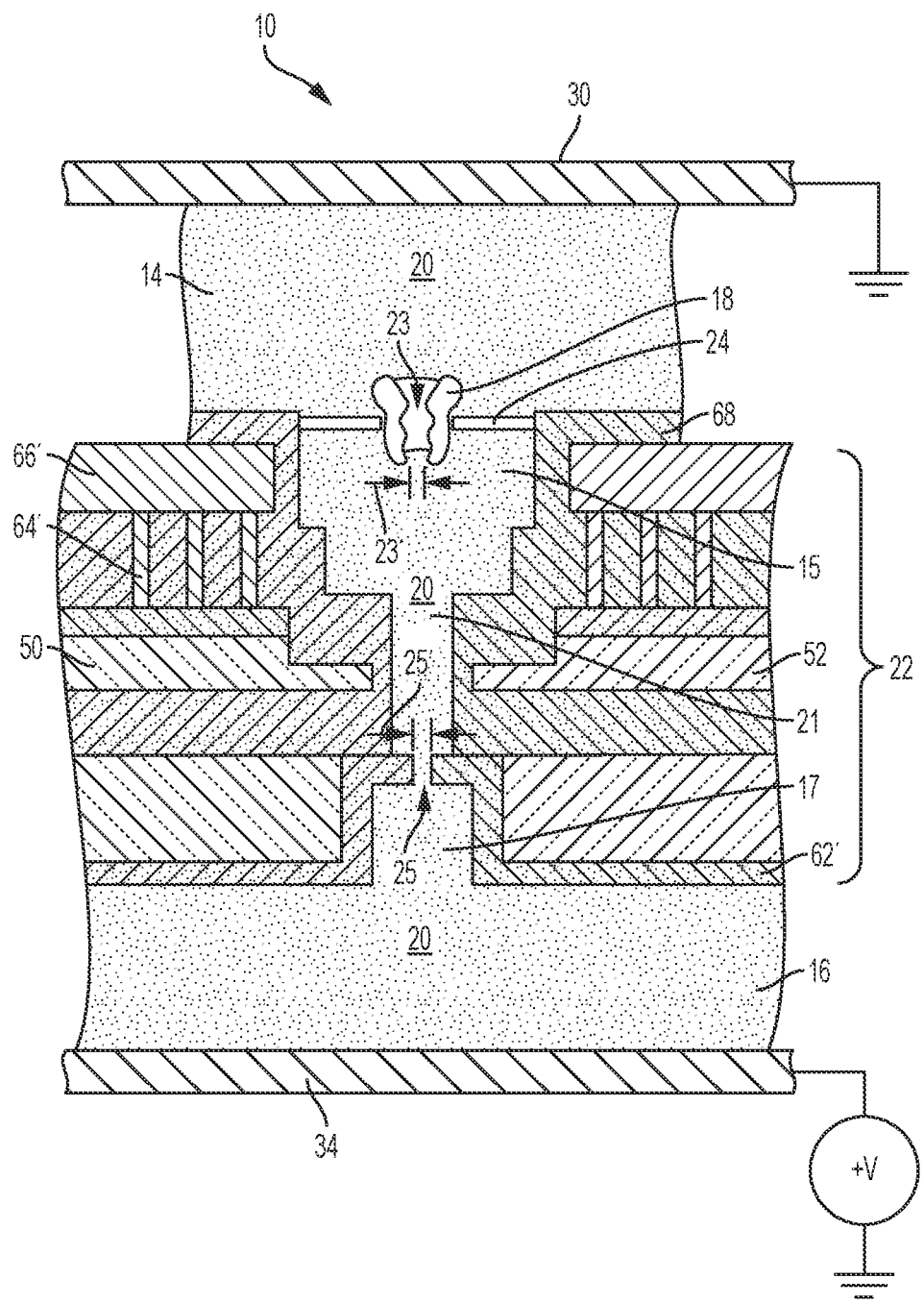
FIG. 2A is a cutaway, schematic and partially cross-sectional view of an example of a device disclosed herein.
Figure 2B:
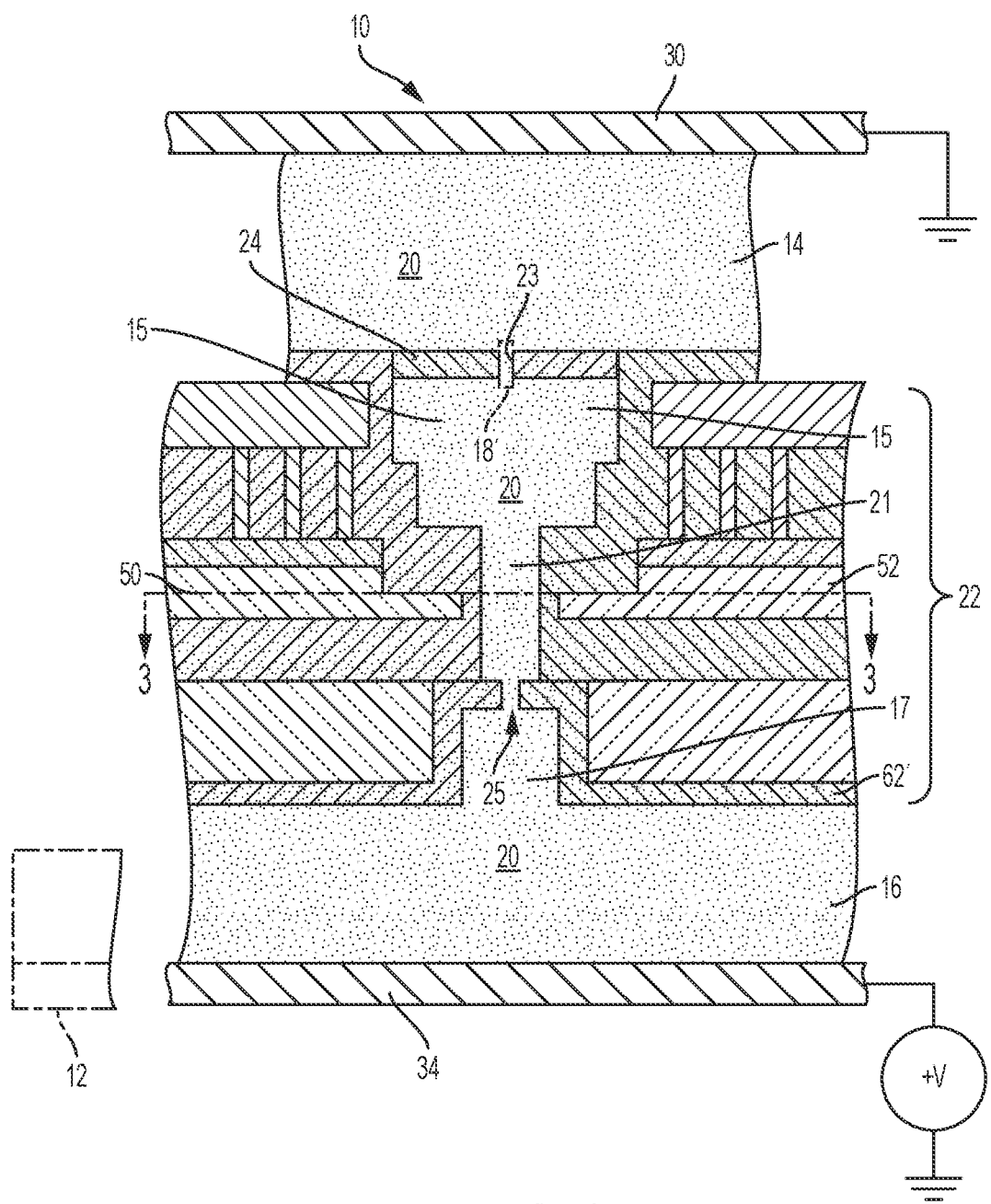
FIG. 2B is a cutaway, schematic and partially cross-sectional view of another example of the device disclosed herein.

Referring now to FIGS. 2A and 2B, a device 10 according to an example of the present disclosure is depicted. The example device 10 includes a cis well 14 associated with a cis electrode 30, a trans well 16 associated with a trans electrode 34, and a field effect transistor (FET) 22 positioned between the cis well 14 and the trans well 16. The FET 22 includes a source 50, a drain 52, and a channel 54 (as seen, for example in FIG. 3).

An example of the FET 22 further includes a fluidic system defined therein. The fluidic system includes a first cavity 15 facing the cis well 14. A second cavity 17 is fluidically connected to the trans well 16, and a through via 21 extends through the FET 22 from the first cavity 15.

The example of device 10 further includes a first nanoscale opening 23 fluidically connecting the cis well 14 and the first cavity 15, the first nanoscale opening 23 having an inner diameter 23'. A second nanoscale opening 25 fluidically connects the through via 21 and the second cavity 17, the second nanoscale opening 25 having an inner diameter 25'. The second nanoscale opening inner diameter 25' is larger than the first nanoscale opening inner diameter 23'.

In an example, the second nanoscale opening inner diameter 25' is at least about two times larger than the first nanoscale opening inner diameter 23'. In another example, the second nanoscale opening inner diameter is about three times larger than the first nanoscale opening inner diameter 23'. In yet another example, the second nanoscale opening inner diameter 25' ranges from about two times larger than the first nanoscale opening inner diameter 23' to about five times larger than the first nanoscale opening inner diameter 23'.

In an example, the area of the second nanoscale opening 25 ranges from about five times to about 10 times larger than the area of the first nanoscale opening 23.

Further, in an example, the first nanoscale opening inner diameter 23' ranges from about 0.5 nm to about 3 nm, and the second nanoscale opening inner diameter 25' ranges from about 10 nm to about 20 nm. In another example, the first nanoscale opening inner diameter 23' ranges from about 1 nm to about 2 nm, and the second nanoscale opening inner diameter 25' ranges from about 10 nm to about 20 nm. In yet another example, the first nanoscale opening inner diameter 23' ranges from about 1 nm to about 3 nm, and the second nanoscale opening inner diameter 25' ranges from about 2 nm to about 20 nm.

An example device 10 further includes a membrane 24 positioned between the cis well 14 and the first cavity 15. The first nanoscale opening 23 extends through the membrane 24. It is to be understood that the membrane 24 may be formed from any suitable natural or synthetic material, as described herein. In an example, the membrane 24 is selected from the group consisting of a lipid and a biomimetic equivalent of a lipid, examples of which are discussed above. In a further example, the membrane 24 is a synthetic membrane (e.g., a solid state membrane, one example of which is silicon nitride), and the first nanoscale opening 23 is a solid state nanopore 18' extending through the membrane 24, as shown in FIG. 2B.

Figure 3:
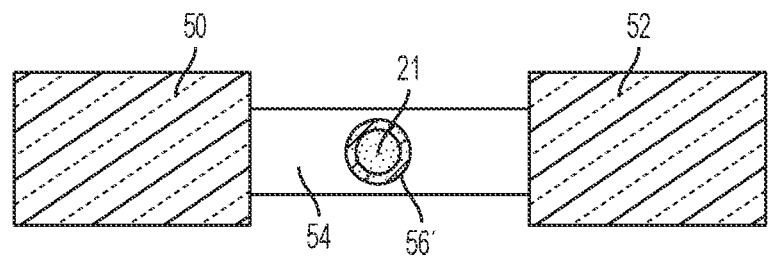
FIG. 3 is a cross-sectional top view, taken on line 3-3 in FIG. 2B, showing an example of a source and drain, gate oxide and through via.

FIG. 3 is a cross-sectional top view, taken on line 3-3 in FIG. 2B, showing an example of the source 50 and drain 52, and the gate oxide 56' on sidewalls of the through via 21. For illustrative purposes in FIG. 3, the insulating material 68 is not shown on the channel 54. The electrolyte 20 in the through via 21 can also be seen (the stippled area in the through via 21) in this view.

In an example, the first nanoscale opening 23 extends through, for example: a polynucleotide nanopore; a polypeptide nanopore; or a carbon nanotube, disposed in the membrane. A polynucleotide nanopore/polypeptide nanopore is shown schematically at 18 in FIG. 2A, and a solid state nanopore, e.g., a carbon nanotube, is shown schematically and in phantom at 18' in FIG. 2B.

In an example, the device 10 is a nanopore sequencer.

A substrate 12 (shown cutaway and in phantom in FIG. 2B) may include a trans well 16 defined therein. In an example, the trans well 16 is fluidically connected to the cis well 14 by the fluidic system of the FET 22 and the respective second 25 and first 23 nanoscale openings. While one common cis well 14 and one common trans well 16 are shown in FIG. 2A, it is to be understood that an array 100 (see, e.g., FIG. 6A) of the devices 10 may include several cis wells 14 that are fluidically isolated from one another and are fluidically connected to respective one or more trans wells 16 fluidically isolated from one another and defined in the substrate 12. Multiple cis wells 14 may be desirable, for example, in order to enable the measurement of multiple samples on a single substrate 12.

Figure 6A:
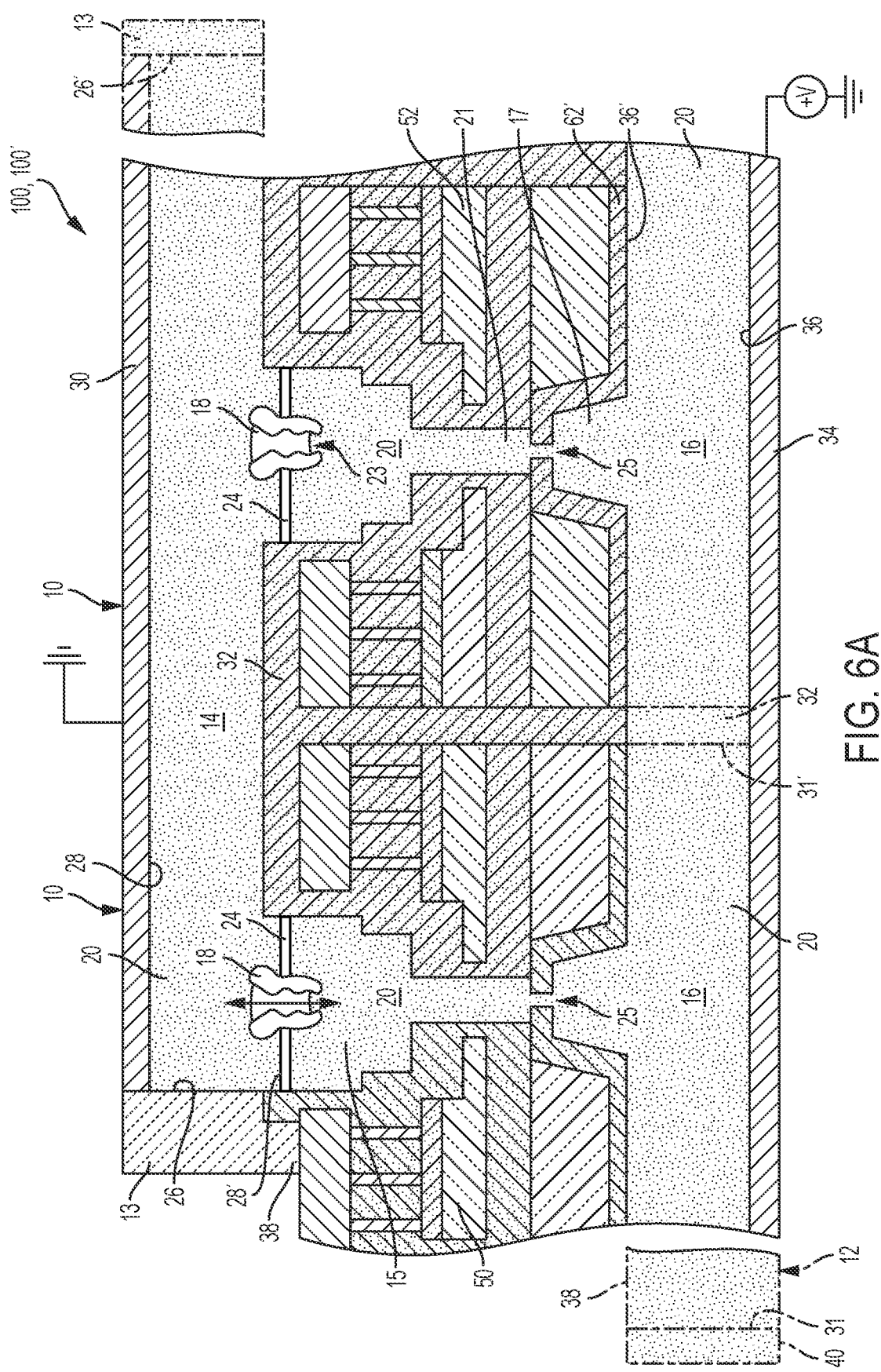
FIG. 6A is a cutaway, schematic and partially cross-sectional view of example arrays of example devices.

The fluid communication through the first nanoscale opening 23/nanopore(s) 18 is indicated by the arrow in FIG. 6A. Also, as shown in FIG. 6A, membrane 24 may be positioned between the cis well 14 and the first cavity 15, and the nanopore(s) 18 may be positioned in, and extend through the membrane 24 to establish the fluidic connection between the cis well 14 and the first cavity 15.

The cis well 14 is a fluid chamber that is defined, e.g., on a portion of a substrate 12 by sidewall(s) 13 that are connected to the substrate 12. In some examples, the sidewall(s) 13 and the substrate 12 may be integrally formed such that they 13, 12 are formed from a continuous piece of material (e.g., glass or plastic). In other examples, the sidewall(s) 13 and the substrate 12 may be separate components that are coupled to each other. In an example, the sidewall(s) 13 are photo patternable polymers.

In the example shown in FIG. 6A, the cis well 14 has interior walls 26, 26' that are defined by the sidewall(s) 13, an upper surface 28 that is defined by a cis electrode 30, and a lower surface 28' that is defined by the membranes 24 and interstitial regions 32. Thus, the cis well 14 is formed within the space defined by the cis electrode 30, the portions of the substrate 12, and the membrane 24. It is to be understood that the lower surface 28' has opening(s) through the first nanoscale openings 23 extending through the membrane 24. The cis well 14 may have any suitable dimensions. In an example, the cis well 14 ranges from about 1 mm×1 mm to about 3 cm×3 cm.

The cis electrode 30, whose interior surface is the upper surface 28 of the cis well 14, may be physically connected to the sidewall(s) 13. The cis electrode 30 may be physically connected to the sidewall(s) 13, for example, by an adhesive or another suitable fastening mechanism. The interface between the cis electrode 30 and the sidewall(s) 13 may seal the upper portion of the cis well 14.

The cis electrode 30 that is used depends, at least in part, upon the redox couple in the electrolyte 20. As examples, the cis electrode 30 may be gold (Au), platinum (Pt), carbon (C) (e.g., graphite, diamond, etc.), palladium (Pd), silver (Ag), copper (Cu), or the like. In an example, the cis electrode 30 may be a silver/silver chloride (Ag/AgCl) electrode.

The cis well 14 is capable of maintaining the electrolyte 20 in contact with the first nanoscale opening 23. In an example, the cis well 14 is in contact with an array of nanopores 18, and thus is capable of maintaining the electrolyte 20 in contact with each of the nanopores 18 in the array.

As illustrated in FIG. 6A, the device 10/array 100 includes a common trans well 16. The trans well 16 is a fluid chamber that may be defined in a portion of the substrate 12. The trans well 16 may extend through the thickness of the substrate 12 and may have openings at opposed ends (e.g., a top end 38 and a bottom end 40) of the substrate 12. In a further example device 10/array 100', as shown in phantom in FIG. 6A, there are two or more trans wells 16. Each trans well 16 has sidewalls 31, 31' that are defined by the substrate 12 and/or by interstitial regions 32 of the substrate 12, a lower surface 36 that is defined by a trans electrode 34, and an upper surface 36' that is defined by base substrate 62' (discussed in further detail below). Thus, each trans well 16 is formed within the space defined by the trans electrode 34, the other portion and/or interstitial regions 32 of the substrate 12, and the base substrate 62'. It is to be understood that the upper surface 36' includes the second nanoscale opening(s) 25 through the base substrate 62' to provide fluid communication to the fluidic system of the FET 22.

The trans electrode 34, whose interior surface is the lower surface 36 of the trans well 16, may be physically connected to the substrate 12 (e.g., to the interstitial regions 32 (if present) or to an interior wall of the substrate 12). The trans electrode 34 may be fabricated in the process of forming the substrate 12 (e.g., during the formation of the trans wells 16). Microfabrication techniques that may be used to form the substrate 12 and the trans electrode 34 include lithography, metal deposition and liftoff, dry and/or spin on film deposition, etching, etc. The interface between the trans electrode 34 and the substrate 12 may seal the lower portion of the trans well 16.

The trans electrode 34 that is used depends, at least in part, upon the redox couple in the electrolyte 20. As examples, the trans electrode 34 may be gold (Au), platinum (Pt), carbon (C) (e.g., graphite, diamond, etc.), palladium (Pd), silver (Ag), copper (Cu), or the like. In an example, the trans electrode 34 may be a silver/silver chloride (Ag/AgCl) electrode.

Many different layouts of the first nanoscale openings 23 may be envisaged, including regular, repeating, and non-regular patterns. In an example, the first nanoscale openings 23 are disposed in a hexagonal grid for close packing and improved density. Other layouts may include, for example, rectilinear (i.e., rectangular) layouts, triangular layouts, and so forth. As examples, the layout or pattern can be an x-y format of first nanoscale openings 23 that are in rows and columns. In some other examples, the layout or pattern can be a repeating arrangement of first nanoscale openings 23 and/or interstitial regions 32. In still other examples, the layout or pattern can be a random arrangement of first nanoscale openings 23 and/or interstitial regions 32. The pattern may include spots, posts, stripes, swirls, lines, triangles, rectangles, circles, arcs, checks, plaids, diagonals, arrows, squares, and/or cross-hatches.

The layout may be characterized with respect to the density of the first nanoscale openings 23 (i.e., number of first nanoscale openings 23 in a defined area of the substrate 12). For example, the first nanoscale openings 23 may be present at a density ranging from about 10 first nanoscale openings 23 per $mm^2$ to about 1,000,000 first nanoscale openings 23 per $mm^2$. The density may be tuned to different densities including, for example, a density of at least about 10 per $mm^2$, about 5,000 per $mm^2$, about 10,000 per $mm^2$, about 0.1 million per $mm^2$, or more. Alternatively or additionally, the density may be tuned to be no more than about 1,000,000 wells per $mm^2$, about 0.1 million per $mm^2$, about 10,000 per $mm^2$, about 5,000 per $mm^2$, or less. It is to be further understood that the density of the first nanoscale openings 23 in the substrate 12 can be between one of the lower values and one of the upper values selected from the ranges above.

The layout may also or alternatively be characterized in terms of the average pitch, i.e., the spacing from the center of a first nanoscale opening 23 to the center of an adjacent first nanoscale opening 23 (center-to-center spacing). The pattern can be regular such that the coefficient of variation around the average pitch is small, or the pattern can be non-regular in which case the coefficient of variation can be relatively large. In an example, the average pitch may range from about 100 nm to about 500 μm. The average pitch can be, for example, at least about 100 nm, about 5 μm, about 10 μm, about 100 μm, or more. Alternatively or additionally, the average pitch can be, for example, at most about 500 μm, about 100 μm, about 50 μm, about 10 μm, about 5 μm, or less. The average pitch for an example array 100 of devices 10 can be between one of the lower values and one of the upper values selected from the ranges above. In an example, the array 100 has a pitch (center-to-center spacing) of about 10 μm. In another example, the array 100 has a pitch (center-to-center spacing) of about 5 μm. In yet another example, the array 100 has a pitch (center-to-center spacing) ranging from about 1 μm to about 10 μm.

The trans wells 16 may be micro wells (having at least one dimension on the micron scale, e.g., about 1 μm up to, but not including, 1000 μm) or nanowells (having at least one dimension on the nanoscale, e.g., about 10 nm up to, but not including, 1000 nm). Each well 16 may be characterized by its aspect ratio (e.g., width or diameter divided by depth or height in this example).

In an example, the aspect ratio of each trans well 16 may range from about 1:1 to about 1:5. In another example, the aspect ratio of each trans well 16 may range from about 1:10 to about 1:50. In an example, the aspect ratio of the trans well 16 is about 3.3.

The depth/height and width/diameter may be selected in order to obtain a desirable aspect ratio. The depth/height of each trans well 16 can be at least about 0.1 μm, about 1 μm, about 10 μm, about 100 μm, or more. Alternatively or additionally, the depth can be at most about 1,000 μm, about 100 μm, about 10 μm, about 1 μm, about 0.1 μm, or less. The width/diameter of each trans well 16 can be at least about 50 nm, about 0.1 μm, about 0.5 μm, about 1 μm, about 10 μm, about 100 μm, or more. Alternatively or additionally, the width/diameter can be at most about 1,000 μm, about 100 μm, about 10 μm, about 1 μm, about 0.5 μm, about 0.1 μm, about 50 nm, or less.

Each trans well 16 has an opening (e.g., fluidically connected to and facing the second cavity 17 of the FET 22) that is large enough to be associated with the second cavity 17.

The cis well 14 and the trans wells 16 may be fabricated using a variety of techniques, including, for example, photolithography, nanoimprint lithography, stamping techniques, embossing techniques, molding techniques, microetching techniques, etc. As will be appreciated by those in the art, the technique used will depend on the composition and shape of the substrate 12 and the sidewall(s) 13. In an example, the cis well 14 may be defined by sidewall(s) 13 at an end 38 of the substrate 12, and the trans wells 16 may be defined through the substrate 12.

The membrane 24 may be any of the non-permeable or semi-permeable materials described herein. The membrane 24 is positioned between the cis well 14 and the first cavity 15, and thus provides a barrier therebetween.

The nanopore(s) 18 may be any of the biological nanopores, solid state nanopores, hybrid nanopores, and synthetic nanopores described herein. As mentioned herein, each nanopore 18 fluidically connects the first cavity 15 to the cis well 14.

The nanopore 18 has two open ends and a hollow core or hole (i.e., the first nanoscale opening 23) that connects the two open ends. When inserted into the membrane 24, one of the open ends of the nanopore 18 faces the cis well 14 and the other of the open ends of the nanopore 18 faces the first cavity 15. In some instances, the open end of the nanopore 18 that faces the first cavity 15 is fluidically connected to the through via 21 and may also be aligned with at least a portion of the through via 21. In other instances, the open end of the nanopore 18 that faces the first cavity 15 is fluidically connected to the through via 21, but is not aligned with the through via 21. The hollow core of the nanopore 18 enables the fluidic and electrical connection between the cis well 14 and the first cavity 15. The diameter of the hollow core may range from about 1 nm up to 1 μm, and may vary along the length of the nanopore 18. In some examples, the open end that faces the cis well 14 may be larger than the open end that faces the cavity 15. In other examples, the open end that faces the cis well 14 may be smaller than the open end that faces the first cavity 15. In any event, the example ranges for the first nanoscale opening inner diameter 23' given above are intended to be the smallest diameter of the nanoscale opening 23 through the nanopore 18.

The nanopore(s) 18 may be inserted into the membrane 24, or the membrane 24 may be formed around the nanopore(s) 18. In an example, the nanopore 18 may insert itself into a formed lipid bilayer (one example of the membrane 24). For example, a nanopore 18 in its monomeric form or polymeric form (e.g., an octamer) may insert itself into the lipid bilayer and assemble into a transmembrane pore. In another example, the nanopore 18 may be added to a grounded side of a lipid bilayer at a desirable concentration where it will insert itself into the lipid bilayer. In still another example, the lipid bilayer may be formed across an aperture in a polytetrafluoroethylene (PTFE) film and positioned between the cis well 14 and the first cavity 15. The nanopore 18 may be added to the grounded cis compartment, and may insert itself into the lipid bilayer at the area where the PTFE aperture is formed. In yet a further example, the nanopore 18 may be tethered to a solid support (e.g., silicon, silicon oxide, quartz, indium tin oxide, gold, polymer, etc.). A tethering molecule, which may be part of the nanopore 18 itself or may be attached to the nanopore 18, may attach the nanopore 18 to the solid support. The attachment via the tethering molecule may be such that a single pore 18 is immobilized (e.g., between the cis well 14 and the first cavity 15). A lipid bilayer may then be formed around the nanopore 18.

Examples of the device 10 include the electrolyte 20 in the cis well 14, the first cavity 15, the through via 21, the second cavity 17, and the trans well 16. The electrolyte 20 may be any electrolyte that is capable of dissociating into counter ions (a cation and its associated anion). As examples, the electrolyte may be any electrolyte that is capable of dissociating into a potassium cation ($K^+$) or a sodium cation ($Na^+$). This type of electrolyte includes a potassium cation and an associated anion, or a sodium cation and an associated anion, or combinations thereof. Examples of potassium-containing electrolytes include potassium chloride (KCl), potassium ferricyanide ($K_3[Fe(CN)_6] \cdot 3H_2O$ or $K_4[Fe(CN)_6] \cdot 3H_2O$), or other potassium-containing electrolytes (e.g., bicarbonate ($KHCO_3$) or phosphates (e.g., $KH_2PO_4$, $K_2HPO_4$, $K_3PO_4$). Examples of sodium-containing electrolytes include sodium chloride (NaCl) or other sodium-containing electrolytes, such as sodium bicarbonate ($NaHCO_3$), sodium phosphates (e.g., $NaH_2PO_4$, $Na_2HPO_4$ or $Na_3PO_4$). As another example, the electrolyte may be any electrolyte that is capable of dissociating into a ruthenium-containing cation (e.g., ruthenium hexamine, such as $[Ru(NH_3)_6]^{2+}$ or $[Ru(NH_3)_6]^{3+}$). Electrolytes that are capable of dissociating into a lithium cation ($Li^+$), a rubidium cation ($Rb^+$), a magnesium cation ($Mg^+$), or a calcium cation ($Ca^+$) may also be used.

Figure 6B:
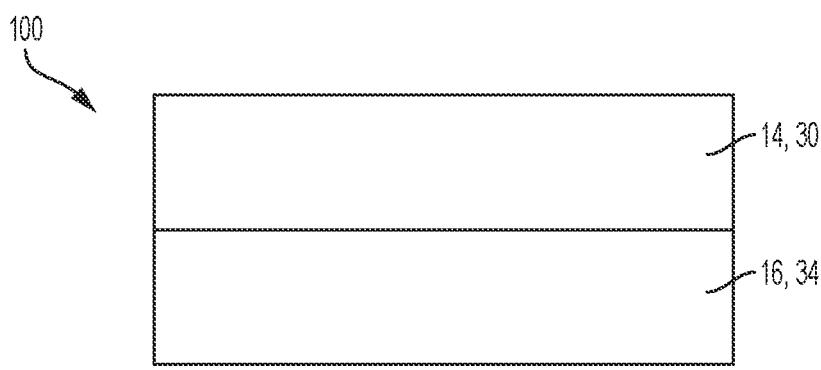
FIGS. 6B-6E are schematic block diagrams of example configurations of arrays of example devices.
Figure 6C:
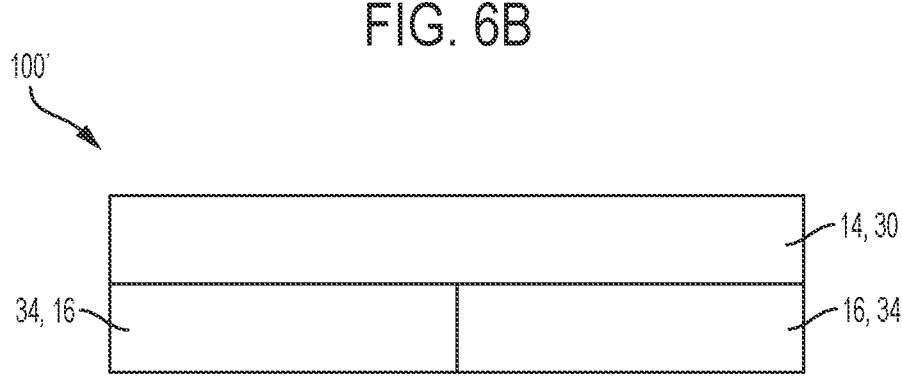
Figure 6D:
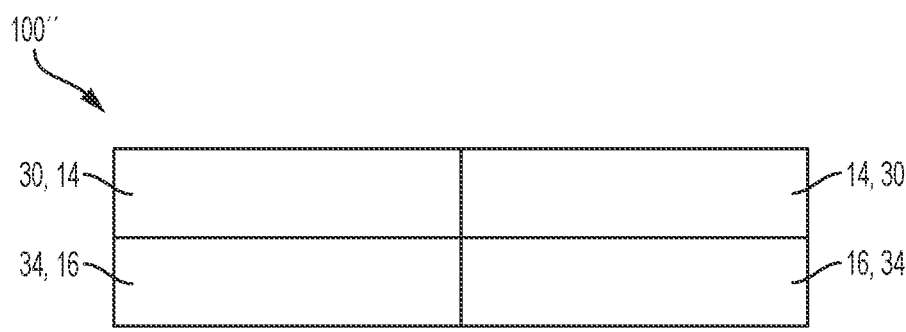
Figure 6E:
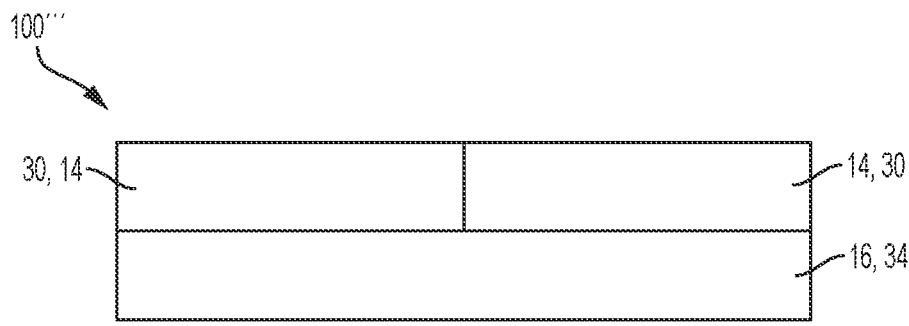

Referring again to FIG. 6A, there is schematically shown an array 100 of devices 10. As mentioned, the devices 10 may be nanopore sequencers. In an example of array 100, each of the plurality of the devices 10/nanopore sequencers shares a common cis electrode 30 and a common trans electrode 34, as schematically shown in FIGS. 6A and 6B. In another example of array 100', each of the plurality of the devices 10/nanopore sequencers shares a common cis electrode 30 and has a distinct trans electrode 34, as schematically shown in FIGS. 6A and 6C. In yet another example of array 100", each of the plurality of the devices 10/nanopore sequencers has a distinct cis electrode 30 and a distinct trans electrode 34, as schematically shown in FIG. 6D. In still another example of array 100''', each of the plurality of the devices 10/nanopore sequencers has a distinct cis electrode 30 and shares a common trans electrode 34, as schematically shown in FIG. 6E.

Figure 4:
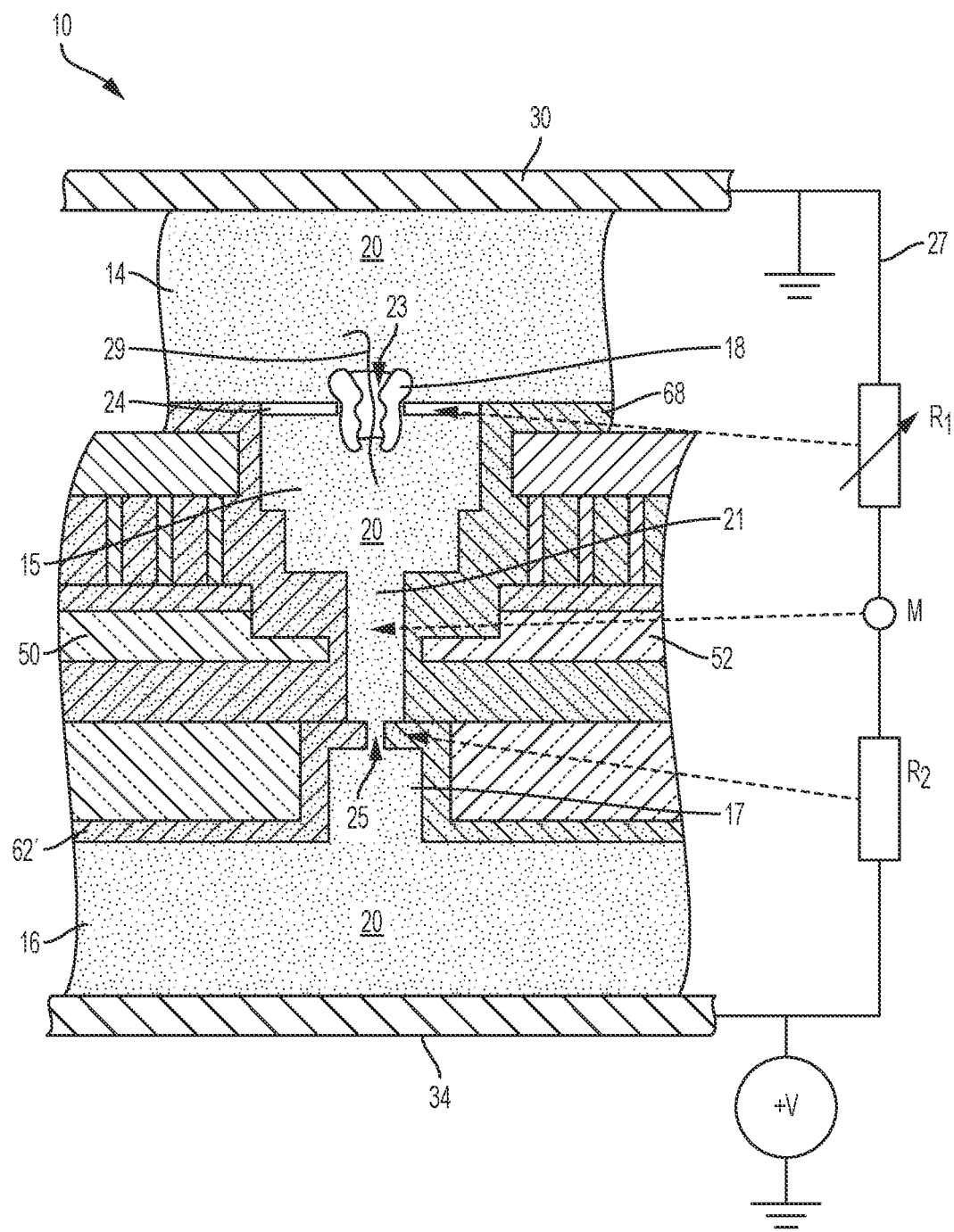
FIG. 4 is a cutaway, schematic and partially cross-sectional view of the example of the device of FIG. 2A, schematically shown in use.
Figure 7:
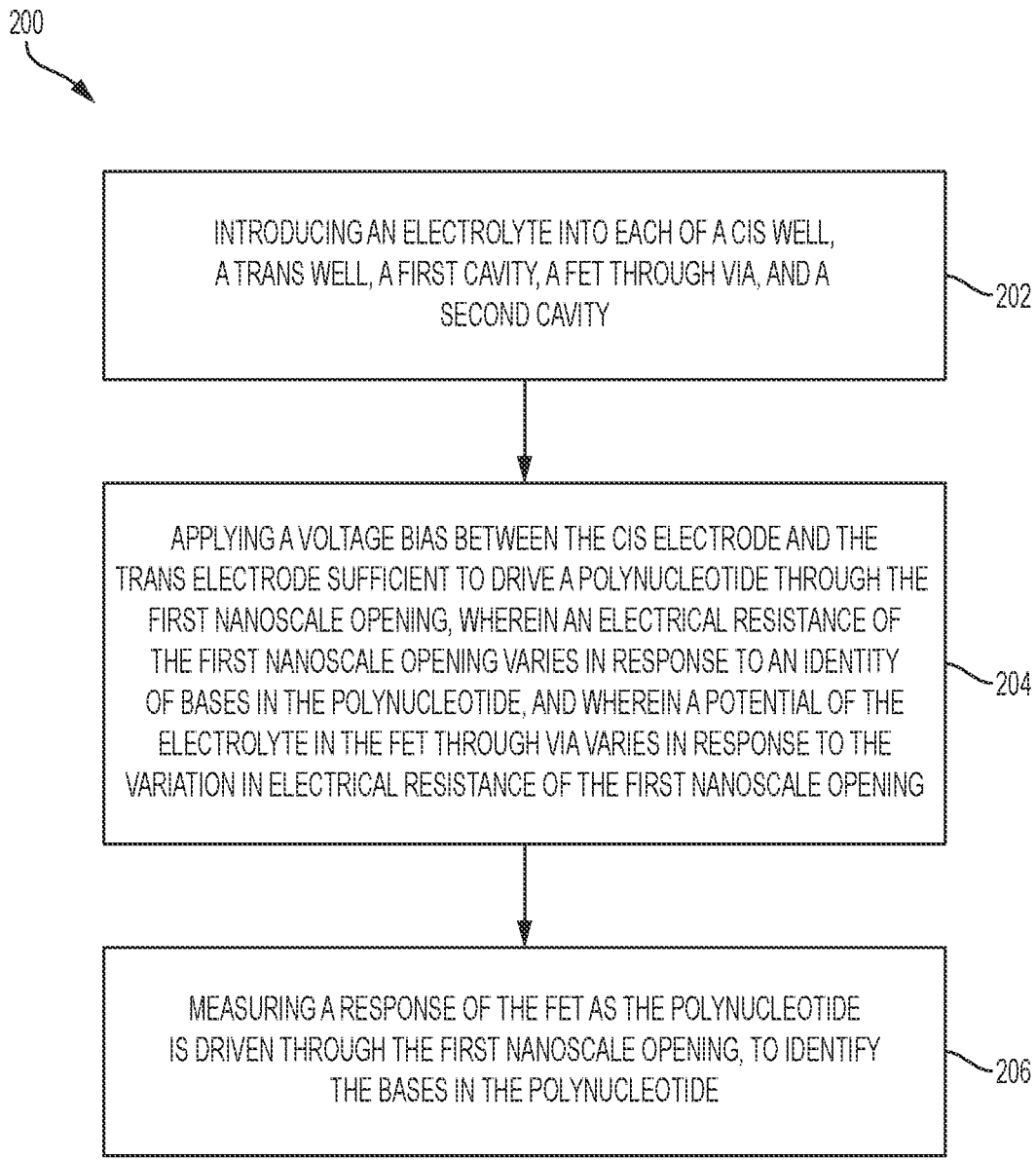
FIG. 7 is a flow diagram illustrating an example of the method disclosed herein involving the device of FIG. 4.

Referring now to FIGS. 4 and 7, an equivalent circuit diagram and operating principle/method 200 of using an example of the device 10 is shown. An electrolyte 20 is introduced into each of the cis well 14, the trans well 16, the first cavity 15, the FET through via 21, and the second cavity 17 (shown at box 202 in FIG. 7). A voltage bias 27 is applied between the cis electrode 30 and the trans electrode 34 sufficient to drive a polynucleotide 29 through the first nanoscale opening 23. An electrical resistance $R_1$ of the first nanoscale opening 23 varies in response to an identity of bases in the polynucleotide 29. A potential of the electrolyte 20 in the FET through via 21 varies in response to the variation in electrical resistance $R_1$ of the first nanoscale opening 23 (shown at box 204 in FIG. 7). The example method 200 further includes measuring a response of the FET 22 as the polynucleotide 29 is driven through the first nanoscale opening 23, to identify the bases in the polynucleotide 29 (shown at box 206 in FIG. 7).

The method 200 may be performed during a nanopore sequencing operation. The application of the electrical potential (i.e., the bias provided by the cis and trans electrodes 30, 34 as the current source) across the nanopore 18 forces the translocation of a nucleotide 29 through the nanopore 18 along with the anions carrying the charge. Depending upon the bias, the nucleotide 29 may be transported from the cis well 14 to first cavity 15, or from the first cavity 15 to the cis well 14. As the nucleotide 29 transits through the nanopores 18, the current across the barrier changes due, for example, to base-dependent blockage of the constriction, for example. The signal from that change in current can be measured using the FET 22.

The range for the voltage can be selected from about −1 V to upwards of about 1 V. The voltage polarity is typically applied such that the negatively charged nucleic acid is electrophoretically driven into the nanopores 18. In some instances, the voltage can be reduced, or the polarity reversed, to facilitate appropriate function.

In an example of the device 10, the first nanoscale opening 23 has a variable electrical resistance $R_1$ as mentioned above. The second nanoscale opening 25 has a fixed, or an at least substantially fixed electrical resistance $R_2$.

Examples of measuring the response of the FET 22 include: measuring a source 50-drain 52 current; or measuring a potential at the source 50 and/or drain 52; or measuring a resistance of the channel 54; or combinations thereof.

In a non-limiting example, the resistance of the first nanoscale opening 23/nanopore 18, $R_1$ may be about 0.5 to about 1 giga-ohm (GΩ), and the resistance of the second nanoscale opening 25, $R_2$ may be about 50 mega-ohm (MΩ). $R_1$ changes as a function of DNA 29 passing through the first nanoscale opening 23.

The potential of the voltage divider point M varies with $R_1$ and modulates the potential at the FET gate 51. The resistance $R_2$ of the second nanoscale opening 25, which may be a solid state nanopore, is fixed or at least substantially fixed and is not modulated by the DNA 29 passing through the first nanoscale opening 23.

As DNA 29 enters the constriction of the first nanoscale opening 23, the resistance $R_1$ of the first nanoscale opening 23 is modulated based on the identity of the bases in the DNA strand 29. The resistance $R_1$ is large and varies by 30-40% when different DNA bases pass through the first nanoscale opening 23. The resistance $R_2$ of the much larger second nanoscale opening 25/solid state nanopore is about 10 times lower and approximately fixed (does not vary), as stated above.

The resulting structure is a voltage divider, where the potential of point M is the potential of the electrolyte 20 in the through via 21. This potential is the equivalent gate potential of the FET 22 and establishes its operating point. As the potential of point M changes with base identity, the current flowing through the FET 22 changes, providing a measurement of the current flowing through the first nanoscale opening 23, and therefore of the identity of DNA bases.

In a nanopore sensor array A (such as that shown in FIG. 1A) the trans electrode 34 is used both to drive the DNA through the nanopore 18, as well as to read out the current associated with the nanopore 18. Therefore, one trans electrode 34 per nanopore 18 is needed, with the resulting limitations on scalability discussed earlier. In contrast, in an example device 10 as disclosed herein, the trans electrode 34 is used to drive the DNA 29 through the first nanoscale opening 23, but the response (e.g., current at the source-drain) to the DNA 29 translocating through the first nanoscale opening 23 is read out with a FET 22 sensor (not the trans electrode 34).

Since the function of the second nanoscale opening 25/solid state nanopore in examples of device 10 is to provide the fixed resistance $R_2$ in the voltage divider (but not to read out the current associated with the first nanoscale opening 23), the second nanoscale opening 25 does not need to be atomically precise.

Further, since individual addressing of the trans electrode 34 is no longer required, in a sensor array 100 the trans well 16 can be larger, thus mitigating the consumption of the electrolyte 20 and the associated limit on sensor lifetime. The scalability of examples of the device 10 is therefore much higher.

As such, the device 10 according to examples of the present disclosure allows for scalability of nanopore sensor arrays 100, for example, by including a larger, common trans well 16 instead of smaller, individually addressable trans wells 16/electrodes 34 by incorporation of a FET 22 and voltage divider.

FIGS. 8A through 8M illustrate an example of a method for making examples of the device 10 disclosed herein. Generally, the method includes fabricating a field effect transistor 22; defining a fluidic system therein, the fluidic system including a first cavity 15 having an inlet end and an outlet end, and a second cavity 17 opposed to the first cavity 15; defining a through via 21 through the field effect transistor 22 from the first cavity outlet end 76 toward the second cavity 17; defining a membrane 24 over the inlet end 76 of the first cavity 15, the membrane 24 having a first nanoscale opening 23 therethrough, the first nanoscale opening 23 having an inner diameter 23'; and defining a second nanoscale opening 25 through a base substrate 62' of the field effect transistor 22 to fluidically connect the through via 21 with the second cavity 17, the second nanoscale opening 25 having an inner diameter 25', wherein the second nanoscale opening inner diameter 25' is larger than the first nanoscale opening inner diameter 23'.

The formation of the field effect transistor 22 is shown in FIGS. 8A through 8H. As will be discussed in FIGS. 8A through 8H, some of the fluidic system components may be formed during the formation of the field effect transistor 22.

Figure 8A:
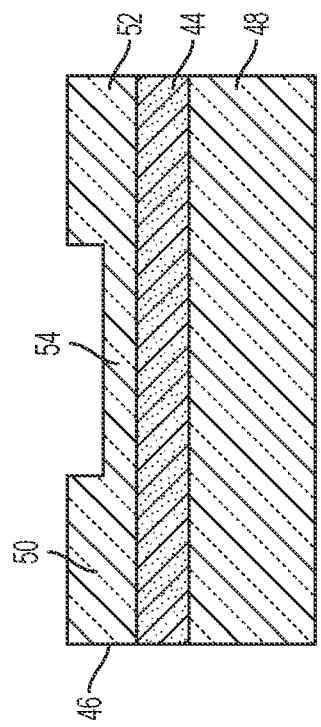
FIGS. 8A-8M together illustrate an example of a method for fabricating an example of a field effect transistor portion of an example of the device.
Figure 8B:
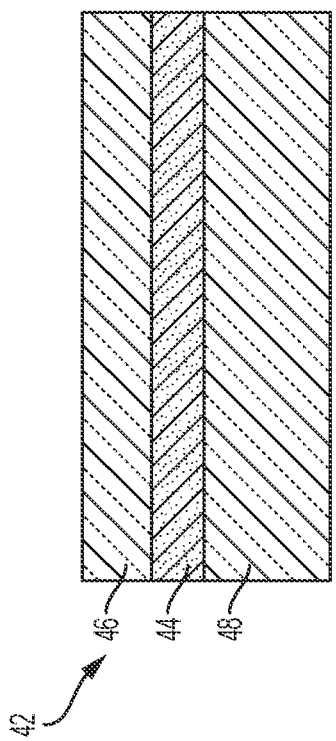
Figure 8C:
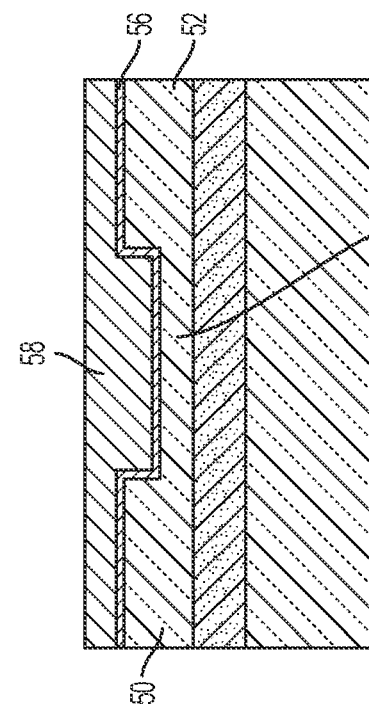

The field effect transistor 22 may be fabricated partially in and/or on a substrate 42, which is shown in FIG. 8A. In some implementations, the substrate 42 may be a silicon on insulator wafer. As shown in FIG. 8A, the silicon on insulator (SOI) substrate 42 is a layered structure including an insulator layer 44 between two silicon layers 46, 48. While a silicon on insulator wafer is shown, it is to be understood that other suitable semiconductor substrates may be used. A source 50, drain 52 and channel 54 may be defined in one of the silicon layers 46 of the substrate 42, as shown in FIG. 8B. The source 50, drain 52 and channel 54 may be formed by patterning (e.g., etching) the silicon layer 46 to desirable depths for each of the components 50, 52, 54. As shown in FIG. 8B, the insulator layer 44 is not exposed during the formation of the source 50, drain 52 and channel 54.

After the source 50, drain 52 and channel 54 are defined, a surface of the silicon layer 46 may be oxidized. This forms a gate oxide 56 on the surface of each of the source 50, drain 52 and channel 54. Oxidation may be accomplished by thermal oxidation, where the substrate 42 is oxidized in a furnace at a temperature ranging from about 700° C. to about 1000° C. Wet or dry thermal oxidation may be used. In an example, the thickness of the gate oxide 56 may be substantially uniform across the source 50, drain 52 and channel 54. In other examples, the gate oxide 56 may be deposited on the source 50, drain 52 and channel 54. Examples of suitable gate oxide materials that may be deposited include $HfO_2$, $Al_2O_3$, $Ta_2O_5$, etc.

Figure 8D:
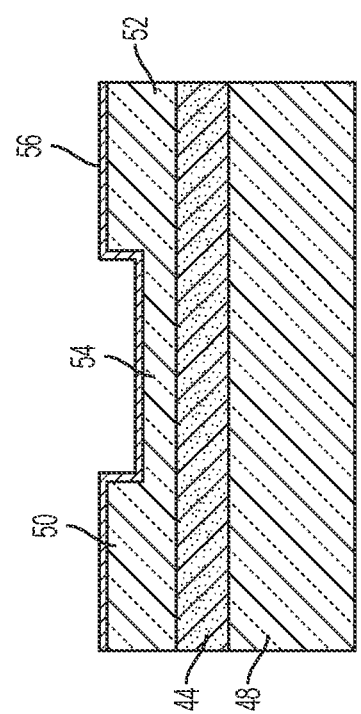
Figure 8E:
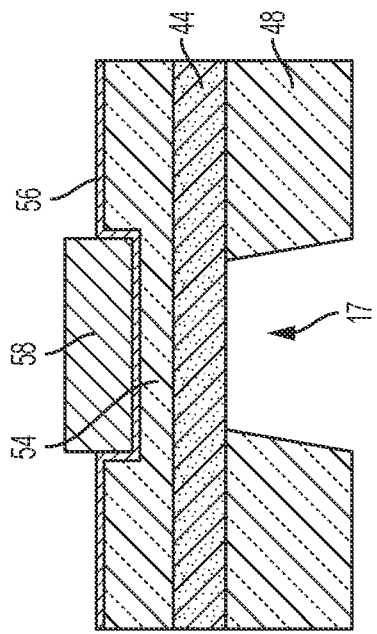

As shown in FIGS. 8D and 8E, the method further involves forming a sacrificial layer 58 on the gate oxide 56 on the channel 54. In an example, the sacrificial layer 58 may be deposited on the entire surface of the gate oxide 56 (as shown in FIG. 8D), and then may be patterned i) to re-expose the source 50 and the drain 52 and the portions of the gate oxide 56 formed thereon, and ii) to leave a portion of the sacrificial layer 58 on the gate oxide 56 formed on the channel 54. Deposition of the sacrificial layer 58 may be accomplished using chemical vapor deposition (CVD) or another suitable deposition technique. Patterning results in the selective removal of the sacrificial layer 58 from the source 50 and drain 52 areas. In an example, patterning may be accomplished using a reactive ion etch process. In another example (not shown), the source 50 and the drain 52 may be covered with a mask, and the sacrificial layer 58 may be deposited on the portion of the gate oxide 56 that overlies the channel 54. Any suitable sacrificial material may be used for the layer 58, such as polysilicon. As shown in FIG. 8E, the sacrificial layer 58 is formed on or remains on (after patterning) the gate oxide 56 that overlies the channel 54.

Figure 8F:
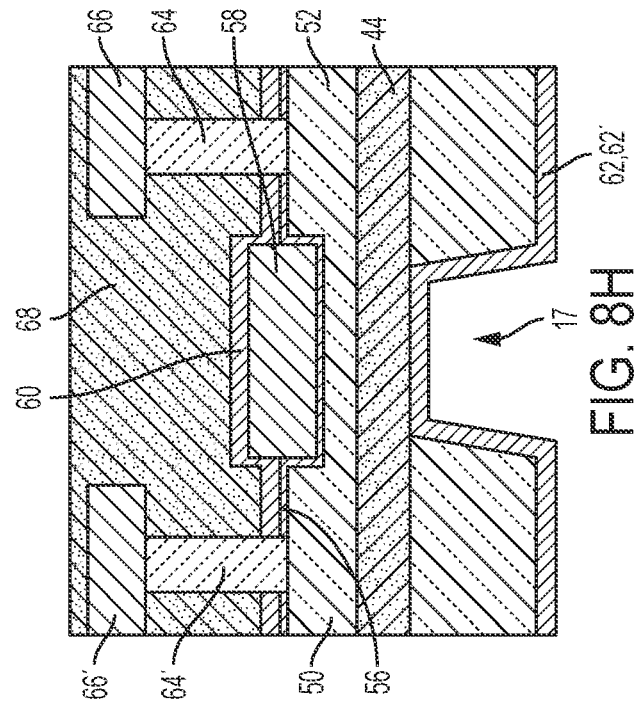

In FIG. 8F, part of the fluidic system is defined. More specifically, the second cavity 17 is defined. In this example, the method includes defining the second cavity 17 of the fluidic system by etching a portion of the second silicon layer 48 of the substrate 42 through to the insulator layer 44 of the substrate 42, wherein the portion etched away is opposed to the channel 54. Any suitable silicon etching technique may be used, such as wet etching (e.g., with tetramethylammonium hydroxide (TMAH), or a mixture of nitric, acetic, and hydrofluoric acids) or dry etching (e.g., with HBr). The dimensions of the second cavity 17 may be relatively large, ranging from about 100 nm to about 1 µm. As illustrated, the sidewalls of the second cavity 17 may be tapered or angled, and thus the dimensions along the depth of the second cavity 17 may vary.

Figure 8G:
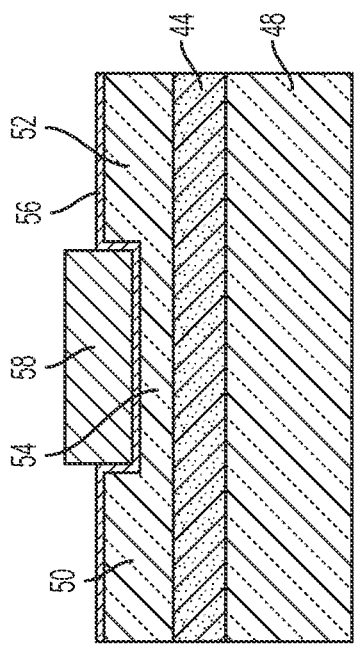
Figure 8H:
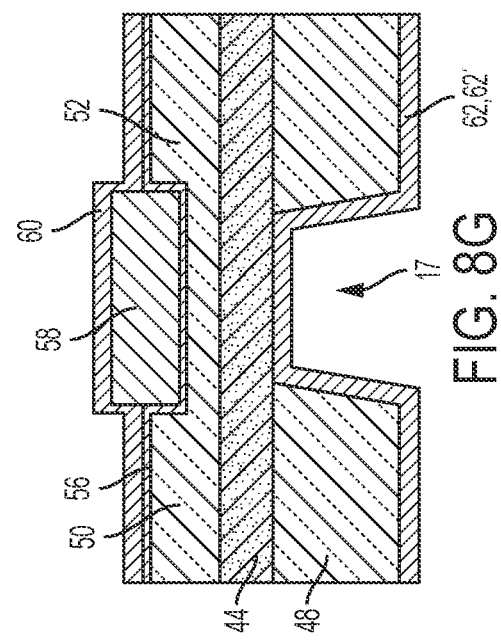

The fabrication of the FET 22 continues in FIGS. 8G and 8H. In FIG. 8G, an etch stop material is deposited to form a layer 60 on the gate oxide 56 (positioned on the source 50 and on the drain 52) and on the sacrificial layer 58, and to form the base substrate 62'. In some examples, the etch stop material may be deposited, e.g., with chemical vapor deposition (CVD), simultaneously on both the front and back surfaces of the structure, as shown in FIG. 8G. In other examples, the etch stop material may be deposited separately to form the layer 60 on the front surfaces of the structure, and to form the base substrate 62' on the back surfaces of the structure. As depicted in FIG. 8G, the etch stop material (which is shown as solid state material 62) deposits on the second silicon layer 48 and on an exposed portion of the insulator layer 44 to form the base substrate 62' (of the FET 22). Examples of the etch stop material for layer 60 and base substrate 62' include silicon nitride ($Si_3N_4$), silicon carbide (SiC), aluminum oxide ($Al_2O_3$), hafnium oxide ($HfO_2$), and tantalum pentoxide ($Ta_2O_5$). Examples of suitable deposition techniques for these materials, in addition to CVD, include atomic layer deposition (ALD), or the like.

As shown in FIG. 8H, the remainder of the FET 22, including a vertical interconnect access (via) 64 and a metallic interconnect 66 partially encapsulated in an insulating material 68, may then be fabricated by semiconductor processing methods. The via 64 electrically connects the source 50 and drain 52 of the FET to the metallic interconnect 66. In the example shown in FIG. 8H, respective vias 64, 64' may be formed in respective electrical contact with the source 50 and the drain 52, and respective metallic interconnects 66, 66' may electrically connect the respective vias 64, 64' to external circuitry (not shown). The vias 64, 64' and metallic interconnects 66, 66' may be any suitable metal (e.g., aluminum, copper, tin, tungsten, zinc, gold, nickel, etc.), metal alloy (e.g., AlSiCu), or other conductive material, and the insulating material 68 may be any suitable insulator (e.g., silicon dioxide, $SiO_2$) that has the desired etch differential with the base substrate 62' (as discussed in more detail below).

Figure 8I:
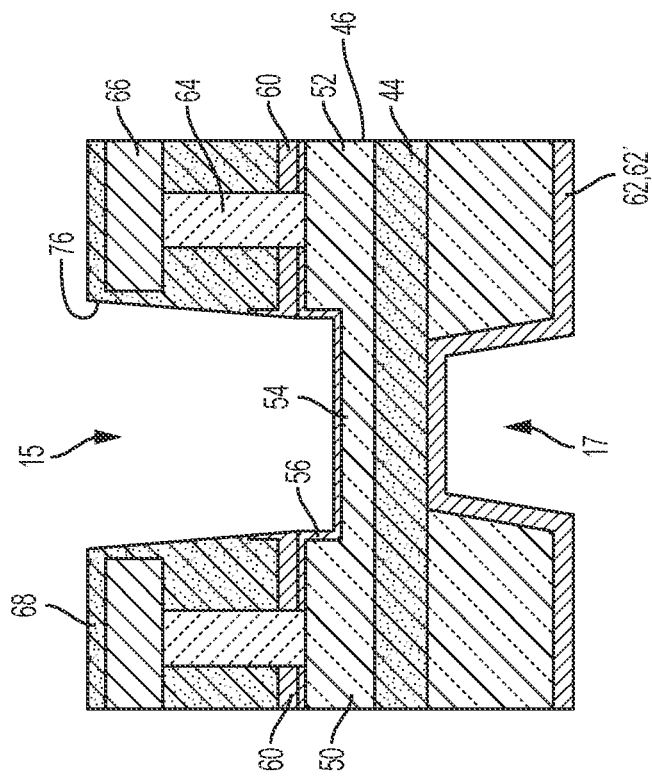
Figure 8J:
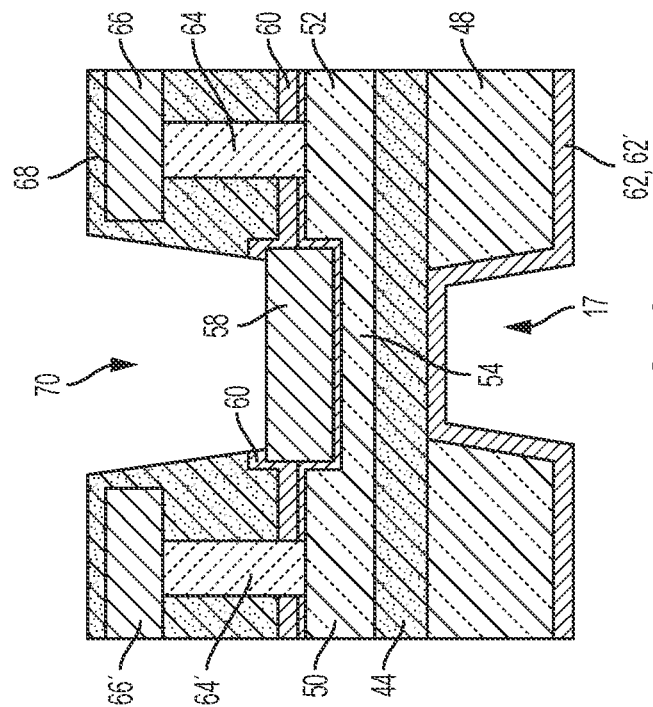

FIGS. 8I and 8J together depict the formation of the first cavity 15 of the fluidic system. Defining the first cavity 15 includes etching an area 70 of the insulating material 68 through to the sacrificial layer 58, wherein the area 70 abuts the channel 54 (FIG. 8I); and etching the sacrificial layer 58 to expose the gate oxide 56 on the channel 54 (FIG. 8J). The etching technique used for each of the insulating material 68 and the sacrificial layer 58 may depend upon the materials 68, 58. When the insulating material 68 is silicon dioxide, etching may be performed, for example, using an etchant with high anisotropy, such as fluorinated reactive ion etch (e.g., $CHF_3/O_2$, $C_2F_6$, $C_3F_8$, and $C_5F_8/CO/O_2/Ar$). The dimensions of the area 70 may be relatively large, for example, up to about 1 µm (e.g., at the inlet end 76 of the first cavity 15). As illustrated, the sidewalls of the area 70 may be tapered inward toward the gate oxide 56), and thus the dimensions along the depth of the area 70 may vary. When the sacrificial layer 58 (FIG. 8I) is polysilicon, etching may be performed, for example, using wet etching or a reactive ion etching process. Etching of the sacrificial layer 58 re-exposes the gate oxide 56 on the channel 54.

Figure 8K:
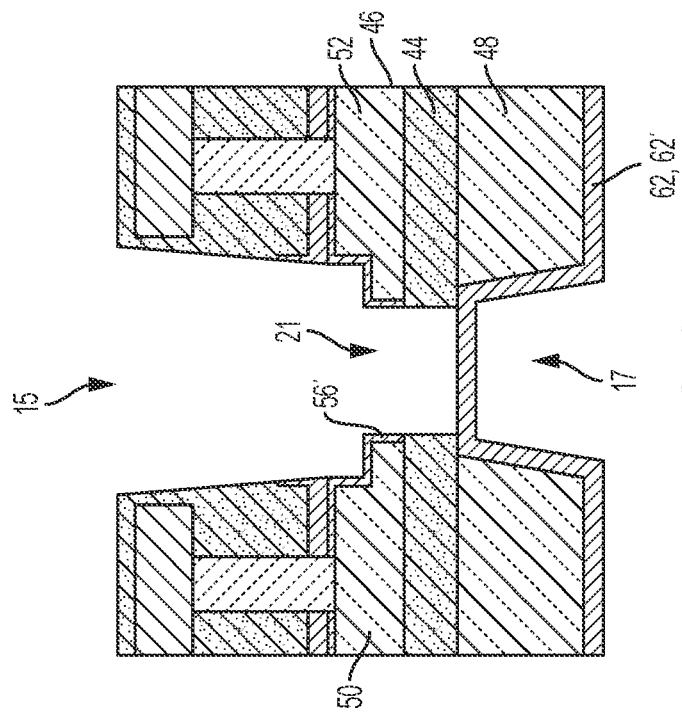

FIG. 8K illustrates the formation of the through via 21. The through via 21 ultimately fluidically connects the first cavity 15 to the second nanoscale opening 25 (see FIG. 8M). As shown in FIG. 8K, defining the through via 21 involves etching through respective portions of each of the gate oxide 56, the silicon layer 46 of the substrate 42, and the insulating layer 44 of the substrate 42 to expose the base substrate 62'/solid state material 62. The etching technique or techniques used will depend upon the materials (e.g., 56, 46, 44) to be etched. The etching technique or etchant used in the technique may be switched when moving from the gate oxide 56, to the silicon layer 46, to the insulating layer 44. In an example, the through via 21 has a diameter ranging from about 35 nm to about 40 nm. In another example, the through via 21 has a diameter of about 40 nm.

As depicted in FIG. 8K, the respective portions of the gate oxide 56, the silicon layer 46, and the insulating layer 44 that are removed to create an opening through the channel 54 and other layers (e.g., 56, 44) of the FET 22. This opening, i.e., through via 21, is in fluid communication with the first cavity 15 through the outlet end 72 of the first cavity 15.

Figure 8L:
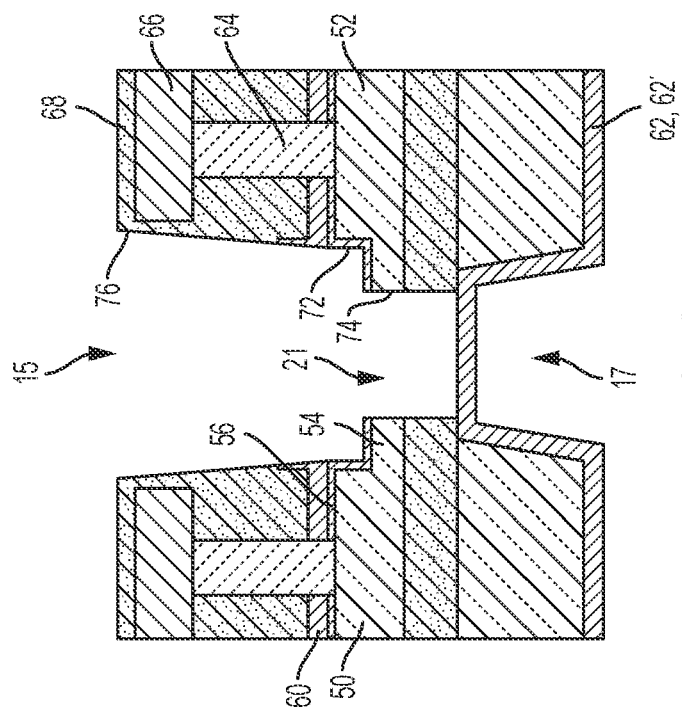

FIG. 8L depicts the formation of an insulating layer 56' on the exposed portions 74 of the channel 54/silicon layer 46. In some examples, the insulating layer 56' is formed by the oxidation of the exposed portions 74 of the silicon layer 46 of the substrate 42 in the through via 21. This oxidation may be achieved using thermal oxidation. While the oxidation of the exposed portions 74 is shown in FIG. 8L; it is to be understood that when thermal oxidation is utilized, it may be desirable to form the through via 21 and oxidize the portions 74 before fabricating the vias 64, 64' and the metallic interconnects 66, 66', as these components may be vulnerable to the heating conditions of thermal oxidation. In other examples, the insulating layer 56' is formed by depositing or growing the insulating layer 56' on the exposed portions 74 of the silicon layer 46 of the substrate 42 in the through via 21. When deposition or growing techniques are used to form the insulating layer 56' on the exposed portions 74, these techniques may take place after the fabrication of the vias 64, 64' and metallic interconnects 66, 66' (as shown), or may take place prior to the fabrication of the vias 64, 64' and metallic interconnects 66, 66'. Fabricating the through via 21 and the insulating layer 56' prior to the vias 64, 64' and metallic interconnects 66, 66' may be particularly desirable when the insulating layer 56' is to be exposed to high temperature oxidation for formation, or high temperature annealing (e.g., from about 700° C. to about 1000° C.) for densification.

Figure 8M:
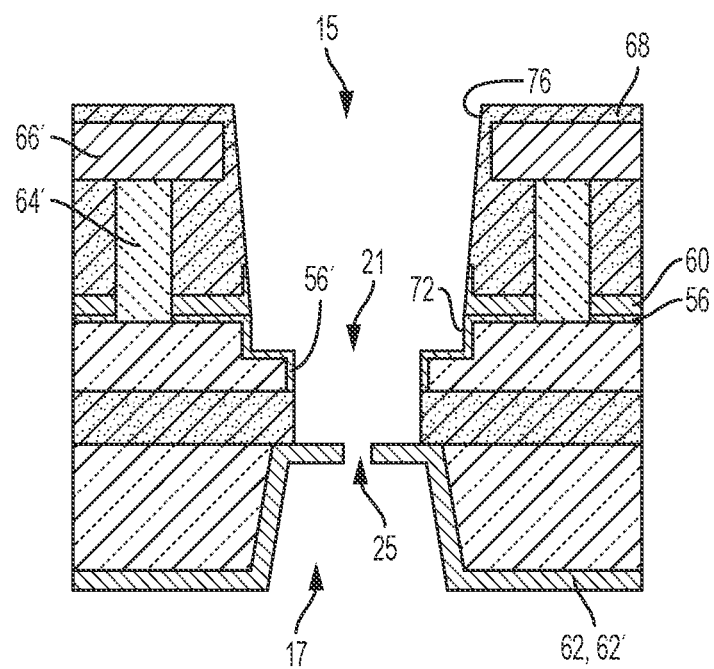

As mentioned above, the method includes defining the second nanoscale opening 25 through the base substrate 62' (i.e., solid state material 62) of the field effect transistor 22 to fluidically connect the through via 21 with the second cavity 17, where the second nanoscale opening 25 has an inner diameter 25' and where the second nanoscale opening inner diameter 25' is larger than an inner diameter 23' of the first nanoscale opening 23 (see, e.g., FIGS. 2A and 2B). The formation of the second nanoscale opening 25 is shown in FIG. 8M. As depicted, the second nanoscale opening 25 is defined in the solid state material 62 (i.e., base substrate 62'). The second nanoscale opening 25 may be defined by etching (using a suitable etchant for the etch stop material used to form the base substrate 62') or ion milling through a portion of the base substrate 62'. The portion that is etched extends through the thickness of the base substrate 62' so that the opening 25 that is formed fluidically connects the through via 21 and the second cavity 17. In an example, the inner diameter 25' of the second nanoscale opening 25 ranges from about 5 nm to about 10 nm.

When fabricating the device 10, it is to be understood that the materials for the etch stop material (which forms the layer 60 and the base substrate 62') and for the insulating layer 68 of the FET 22 are selected so that there is a significant etch differential between the materials. The etching rate of the insulating layer 68 should be higher than the etching rate of the etch stop material (i.e., layer 60 and base substrate 62'). Examples of suitable material combinations for the etch stop material (i.e., layer 60 and base substrate 62') and the insulating layer 68 which provide a suitable etch differential include $Si_3N_4$ (layer 60 and base substrate 62') and $SiO_2$ (insulating layer 68) or SiC (layer 60 and base substrate 62') and $Al_2O_3$ (insulating layer 68).

While not shown in FIGS. 8A through 8M, examples of the method further include the formation of the first nanoscale opening 23 (FIGS. 2A and 2B). As shown in FIG. 8M, the first cavity 15 has an inlet end 76 (which is opposed to the outlet end 72). A membrane 24 (FIGS. 2A and 2B) may be defined over the inlet end 76 of the first cavity 15. The membrane 24 has the first nanoscale opening 23 therethrough, and the first nanoscale opening 23 has the inner diameter 23'. The technique(s) used to form the membrane 24 and the first nanoscale opening 23 may depend on the type of membrane 24 and nanoscale opening 23 that are used. As examples, the nanoscale opening 23 may be inserted into the membrane 24, or the membrane 24 may be formed around the nanoscale opening 23. In an example, the nanoscale opening 23 may insert itself into a formed lipid bilayer (one example of the membrane 24). For example, as mentioned above, a nanoscale opening 23 in its monomeric form or polymeric form (e.g., an octamer) may insert itself into the lipid bilayer and assemble into a transmembrane pore. In another example, the nanoscale opening 23 may be added to a grounded side of a lipid bilayer at a desirable concentration where it will insert itself into the lipid bilayer. In still another example, the lipid bilayer may be formed across an aperture in a polytetrafluoroethylene (PTFE) film and positioned at the inlet end 76 of the first cavity 15. The nanoscale opening 23 may be added to a grounded side of the lipid bilayer, and may insert itself into the lipid bilayer at the area where the PTFE aperture is formed. In yet a further example, the nanoscale opening 23 may be tethered to a solid support (e.g., silicon, silicon oxide, quartz, indium tin oxide, gold, polymer, etc.). A tethering molecule, which may be part of the nanoscale opening 23 itself or may be attached to the nanoscale opening 23, may attach the nanoscale opening 23 to the solid support. The attachment via the tethering molecule may be such that a single nanoscale opening 23 is immobilized at the inlet end 76 of the first cavity 15. A lipid bilayer may then be formed around the nanoscale opening 23. The nanoscale opening 23 may also be a solid state opening. In these examples, another solid state material (e.g., 62) may be deposited over the inlet end 76 and on the insulating material 68. The nanoscale opening 23 may be formed in this solid state material so that its inner diameter has the desirable dimensions as disclosed herein.

Several example techniques have been provided herein for the formation of the device 10. It is to be understood that any of the features of the device 10 having a smallest dimension larger than 40 nm (e.g., first cavity 15, second cavity 17) may be fabricated with conventional (dry) 193 nm lithography.

While not shown, the method may further include fluidically connecting a cis well (e.g., cis well 14, FIGS. 2A and 2B) to the first nanoscale opening 23, the cis well 14 being associated with a cis electrode (e.g., cis electrode 30, FIGS. 2A and 2B); fluidically connecting a trans well (e.g., trans well 16, FIGS. 2A and 2B) to the second cavity 17, the trans well 16 being associated with a trans electrode (e.g., trans electrode 34, FIGS. 2A and 2B), thereby forming an example of device 10 (e.g., a nanopore sequencer); and immersing the nanopore sequencer/device 10 into an electrolyte 20. The configuration of the cis well(s) 14, cis electrode(s) 30, trans well(s) 16, and trans electrode(s) 34 may be in accordance with any of the examples disclosed herein.

As discussed in more detail above, the electrolyte 20 may be any electrolyte that is capable of dissociating into counter ions (a cation and its associated anion).

ADDITIONAL NOTES

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if such value or sub-range were explicitly recited. For example, a range from about 2 nm to about 20 nm should be interpreted to include not only the explicitly recited limits of from about 2 nm to about 20 nm, but also to include individual values, such as about 3.5 nm, about 8 nm, about 18.2 nm, etc., and sub-ranges, such as from about 5 nm to about 10 nm, etc. Furthermore, when "about" and/or "substantially" are/is utilized to describe a value, this is meant to encompass minor variations (up to +/−10%) from the stated value.

While several examples have been described in detail, it is to be understood that the disclosed examples may be modified. Therefore, the foregoing description is to be considered non-limiting.

What is claimed is:

1. A device, comprising:
   a cis well associated with a cis electrode;
   a trans well associated with a trans electrode;
   a field effect transistor (FET) positioned between the cis well and the trans well, the field effect transistor (FET) including:
      a fluidic system defined therein, the fluidic system including:
         a first cavity facing the cis well;
         a second cavity fluidically connected to the trans well; and
         a through via extending through the field effect transistor from the first cavity;
   a membrane positioned between the cis well and the first cavity;
   a first nanoscale opening fluidically connecting the cis well and the first cavity, the first nanoscale opening having an inner diameter, wherein the first nanoscale opening extends through the membrane, and wherein the first nanoscale opening inner diameter ranges from about 0.5 nm to about 3 nm; and
   a second nanoscale opening fluidically connecting the through via and the second cavity, the second nanoscale opening having an inner diameter, wherein the second nanoscale opening inner diameter ranges from about 2 nm to about 20 nm, and wherein the second nanoscale opening inner diameter is at least about two times larger than the first nanoscale opening inner diameter.

2. The device as defined in claim 1, wherein the first nanoscale opening extends through a nanopore; and wherein the nanopore is inserted into the membrane, or the membrane is formed around the nanopore.

3. The device as defined in claim 2, wherein the membrane is a formed lipid bilayer and the nanopore inserts itself into the formed lipid bilayer.

4. The device as defined in claim 3, wherein:
   the nanopore inserts itself in a monomeric form or a polymeric form into the formed lipid bilayer and the nanopore assembles into a transmembrane pore; or
   the nanopore is added to a grounded side of the formed lipid bilayer, and wherein the nanopore inserts itself into the formed lipid bilayer subsequent to the nanopore being added to the grounded side of the formed lipid bilayer.

5. The device as defined in claim 3, wherein the lipid bilayer is formed across an aperture in a polytetrafluoroethylene (PTFE) film and positioned between the cis well and the first cavity; and wherein the nanopore is added to a grounded cis compartment, and the nanopore inserts itself into the lipid bilayer where the aperture in the PTFE film is formed.

6. The device as defined in claim 1, wherein:
   the first nanoscale opening has a variable electrical resistance; and
   the second nanoscale opening has an at least substantially fixed electrical resistance.

7. An array of a plurality of nanopore sequencers, wherein each of the nanopore sequencers comprises:
   a cis well associated with a cis electrode;
   a trans well associated with a trans electrode;
   a field effect transistor (FET) positioned between the cis well and the trans well, the field effect transistor (FET) including:
      a fluidic system defined therein, the fluidic system including:
         a first cavity facing the cis well;
         a second cavity fluidically connected to the trans well; and
         a through via extending through the field effect transistor from the first cavity;
   a membrane positioned between the cis well and the first cavity;
   a first nanoscale opening fluidically connecting the cis well and the first cavity, the first nanoscale opening having an inner diameter, wherein the first nanoscale opening extends through the membrane, and wherein the first nanoscale opening inner diameter ranges from about 0.5 nm to about 3 nm; and
   a second nanoscale opening fluidically connecting the through via and the second cavity, the second nanoscale opening having an inner diameter, wherein the second nanoscale opening inner diameter ranges from about 2 nm to about 20 nm, and wherein the second nanoscale opening inner diameter is at least about two times larger than the first nanoscale opening inner diameter.

8. The array as defined in claim 7, wherein each of the plurality of the nanopore sequencers shares a common cis electrode and a common trans electrode.

9. The array as defined in claim 7, wherein each of the plurality of the nanopore sequencers shares a common cis electrode and has a distinct trans electrode.

10. The array as defined in claim 7, wherein:
    each of the plurality of the nanopore sequencers has a distinct cis electrode and a distinct trans electrode; or
    each of the plurality of the nanopore sequencers has a distinct cis electrode and shares a common trans electrode.

11. The array as defined in claim 7, wherein the second nanoscale opening inner diameter ranges from about two times larger than the first nanoscale opening inner diameter to about five times larger than the first nanoscale opening inner diameter.

12. The array as defined in claim 7, wherein the second nanoscale opening inner diameter ranges from about 10 nm to about 20 nm.

13. The array as defined in claim 7, wherein:
    the first nanoscale opening inner diameter ranges from about 1 nm to about 2 nm; and
    the second nanoscale opening inner diameter ranges from about 10 nm to about 20 nm.

14. The array as defined in claim 7, wherein the membrane is selected from the group consisting of a lipid and a biomimetic equivalent of a lipid.

15. The array as defined in claim 14 wherein the first nanoscale opening extends through: a polynucleotide nanopore; a polypeptide nanopore; or a carbon nanotube, disposed in the membrane.

16. The array as defined in claim 7, wherein the membrane is a synthetic membrane, and wherein the first nanoscale opening is a solid state nanopore.

17. A method of using a device, comprising:
a cis well associated with a cis electrode;
a trans well associated with a trans electrode;
a field effect transistor (FET) positioned between the cis well and the trans well, the field effect transistor (FET) including:
   a fluidic system defined therein, the fluidic system including:
      a first cavity facing the cis well;
      a second cavity fluidically connected to the trans well; and
      a through via extending through the field effect transistor from the first cavity;
a membrane positioned between the cis well and the first cavity;
a first nanoscale opening fluidically connecting the cis well and the first cavity, the first nanoscale opening having an inner diameter, wherein the first nanoscale opening extends through the membrane, and wherein the first nanoscale opening inner diameter ranges from about 0.5 nm to about 3 nm; and
a second nanoscale opening fluidically connecting the through via and the second cavity, the second nanoscale opening having an inner diameter, wherein the second nanoscale opening inner diameter ranges from about 2 nm to about 20 nm, and wherein the second nanoscale opening inner diameter is at least about two times larger than the first nanoscale opening inner diameter;
wherein the method comprises:
introducing an electrolyte into each of the cis well, the trans well, the first cavity, the FET through via, and the second cavity;
applying a voltage bias between the cis electrode and the trans electrode sufficient to drive a polynucleotide through the first nanoscale opening, wherein an electrical resistance of the first nanoscale opening varies in response to an identity of bases in the polynucleotide, and wherein a potential of the electrolyte in the FET through via varies in response to the variation in electrical resistance of the first nanoscale opening; and
measuring a response of the FET as the polynucleotide is driven through the first nanoscale opening, to identify the bases in the polynucleotide.

18. The method as defined in claim 17, wherein the FET further comprises a source, a drain, and a channel, and wherein measuring the response of the FET includes:
measuring a source-drain current; or
measuring a potential at the source, the drain, or both the source and the drain; or
measuring a resistance of the channel; or
combinations thereof.

19. The method as defined in claim 17, wherein:
the first nanoscale opening extends through a nanopore;
the nanopore is inserted into the membrane, or the membrane is formed around the nanopore; and
the nanopore is tethered to a solid support, the solid support comprising: silicon, silicon oxide, quartz, indium tin oxide, gold, or a polymer.

20. The method as defined in claim 19, wherein the nanopore includes a tethering molecule, or the nanopore is attached to the tethering molecule, wherein the tethering molecule is attached to the solid support.

* * * * *